(12) United States Patent
Brahmbhatt et al.

(10) Patent No.: US 11,485,976 B2
(45) Date of Patent: Nov. 1, 2022

(54) BACTERIAL MINICELLS FOR DELIVERING NUCLEIC ACID ADJUVANTS AND METHODS OF USING THE SAME

(71) Applicant: EnGeneIC Molecular Delivery Pty. Ltd., Sydney (AU)

(72) Inventors: Himanshu Brahmbhatt, Sydney (AU); Jennifer MacDiarmid, Sydney (AU)

(73) Assignee: ENGENEIC MOLECULAR DELIVERY PTY LTD, Sydney (AU)

( * ) Notice: Subject to any disclaimer, the term of this patent is extended or adjusted under 35 U.S.C. 154(b) by 20 days.

(21) Appl. No.: 15/725,008

(22) Filed: Oct. 4, 2017

(65) Prior Publication Data

US 2018/0100159 A1 Apr. 12, 2018

Related U.S. Application Data

(60) Provisional application No. 62/405,074, filed on Oct. 6, 2016.

(51) Int. Cl.
| | |
|---|---|
| *C12N 15/63* | (2006.01) |
| *A61P 35/00* | (2006.01) |
| *C07K 16/12* | (2006.01) |
| *A61K 39/39* | (2006.01) |
| *C12N 15/117* | (2010.01) |
| *C07K 16/28* | (2006.01) |
| *A61K 35/74* | (2015.01) |
| *C07K 14/195* | (2006.01) |
| *C12N 15/10* | (2006.01) |
| *C40B 40/02* | (2006.01) |
| *G01N 33/543* | (2006.01) |
| *A61K 39/00* | (2006.01) |
| *C07K 16/00* | (2006.01) |

(52) U.S. Cl.
CPC ............ *C12N 15/63* (2013.01); *A61K 35/74* (2013.01); *A61K 39/39* (2013.01); *A61P 35/00* (2018.01); *C07K 14/195* (2013.01); *C07K 16/1235* (2013.01); *C07K 16/28* (2013.01); *C07K 16/2863* (2013.01); *C12N 15/1034* (2013.01); *C12N 15/117* (2013.01); *C40B 40/02* (2013.01); *G01N 33/543* (2013.01); *A61K 2039/505* (2013.01); *A61K 2039/52* (2013.01); *A61K 2039/55561* (2013.01); *C07K 16/00* (2013.01); *C07K 2317/31* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,037,743 A | 8/1991 | Welch et al. | |
| 5,143,830 A | 9/1992 | Holland et al. | |
| 6,025,197 A | 2/2000 | Sheppard | |
| 7,183,105 B2 | 2/2007 | Sabbadini et al. | |
| 8,591,862 B2 | 11/2013 | Brahmbhatt et al. | |
| 8,772,013 B2* | 7/2014 | Brahmbhatt | A61K 9/0019 |
| | | | 435/252.1 |
| 9,090,650 B2* | 7/2015 | Seya | A61K 31/713 |
| 2003/0232074 A1* | 12/2003 | Lipford | A61K 31/7125 |
| | | | 424/450 |
| 2004/0141950 A1* | 7/2004 | Noelle | A61K 31/4745 |
| | | | 424/85.1 |
| 2007/0298056 A1 | 12/2007 | Brahmbhatt et al. | |
| 2012/0034248 A1* | 2/2012 | Kandimalla | A61K 39/39 |
| | | | 424/184.1 |
| 2012/0142079 A1 | 6/2012 | Saboao et al. | |
| 2012/0207754 A1* | 8/2012 | Giacalone | C12N 1/02 |
| | | | 424/134.1 |
| 2015/0098897 A1 | 4/2015 | Brahmbhatt et al. | |

FOREIGN PATENT DOCUMENTS

| | | |
|---|---|---|
| EP | 2 599 866 A1 | 6/2013 |
| WO | WO 95/21191 | 8/1995 |
| WO | WO 2000/67776 | 11/2000 |
| WO | WO 2003/033519 A2 | 4/2003 |
| WO | WO 2004/113507 A1 | 12/2004 |
| WO | WO 2005/056749 A2 | 6/2005 |
| WO | WO 2005/079854 A1 | 9/2005 |
| WO | WO 2009/027830 A2 | 3/2009 |
| WO | WO2015/049589 A1 | 4/2015 |

OTHER PUBLICATIONS

Advanced Drug Delivery Reviews 65 (2013) 1386-1399.*
Poly(I:C) HMW : https://www.invivogen.com/polyic-hmw retrieved May 31, 2019.*
MacDiarmid et al. Cancer Cells 11, 431-445, May 2007.*
MacDiarmid et al. Cell Cycle 6:17, 2099-2105, Sep. 2007.*
MacDiarmid et al.https://www.researchgate.net/scientific-eontributions/Jennifer-MacDiarmid-34455649. downloaded on Feb. 17, 2021.*
Glas et al., "Targeting cytosolic innate immune receptors RIG-I and MDA5 effectively counteracts cancer cell heterogeneity in glioblastoma." *Stem Cells*, vol. 31. pp. 1064-1074 (2013).
Giacalone, et al., "The use of bacterial minicells to transfer plasmid DNA to eukaryotic calls," vol. 8, No. 10, pp. 1624-1633 (2006).
International Search Report and Written Opinion issued in related International Patent Application No. PCT/IB2017/056131, dated Dec. 28, 2017.
Alexopoulou, et al., "Recognition of double-stranded RNA and activation of NF-κB by Toll-like receptor 3," *Nature*, vol. 413, pp. 732-738 (2001).
Ammi, et al., "Poly(I:C) as cancer vaccine adjuvant: knocking on the door of medical breakthroughs," *Pharmacol. Ther.*, vol. 140, pp. 120-131 (2014).

(Continued)

Primary Examiner — Oluwatosin A Ogunbiyi
(74) Attorney, Agent, or Firm — Foley & Lardner LLP

(57) ABSTRACT

This disclosure provides intact bacterially derived minicells containing nucleic acids adjuvants or plasmids encoding nucleic acids adjuvants that can produce a desired immune response in target cells. This disclosure further provides methods that employ minicells to deliver nucleic acids adjuvants for use in the treatment of diseases, including neoplastic disease and cancer.

21 Claims, 4 Drawing Sheets

(56) References Cited

OTHER PUBLICATIONS

Blasius, "Intracellular toll-like receptors," Immunity 32, pp. 305-315 (2010).
Brazda et al., "Preferential binding of IFI16 protein to cruciform structure and superhelical DNA," Biochem Biophys Res Commun., 422, pp. 716-720 (2012).
Costa et al., "Redistribution of the nuclear protein IFI16 into the cytoplasm of ultraviolet B-exposed keratinocytes as a mechanism of autoantigen processing," Br J Dermatol. 164, pp. 282-290 (2011).
Dawson, et al., "The interferon-inducible autoantigen, IFI 16: localization to the nucleolus and identification of a DNA-binding domain," Biochem Biophys Res Commun. 214, pp. 152-162 (1995).
Diner, et al., "The functional interactome of PYHIN immune regulators reveals IFIX is a sensor of viral DNA," Mol. Syst. Biol. 11, p. 787 (2015).
Diner, BA., Lum KK., Cristea, IM., The emerging role of nuclear viral DNA sensors. J. Biol. Chem. 290, 26412-26421 (2015).
Field, et al., "Inducers of interferon and host resistance. II. Multistranded synthetic polynucleotide complexes," Proc. Natl Acad. Sci. USA 58, pp. 1004-1010 (1967).
Gao, et al., "Cyclic [G(2',5')pA(3',5')p] is the metazoan second messenger produced by DNA-activated cyclic GMP-AMP synthase," Cell 153, pp. 1094-1107 (2013).
Gitlin, et al., "Essential role of mda-5 in type I IFN responses to polyriboinosinic:polyribocytidylic acid and encephalomyocarditis picornavirus," Proc. Natl Acad. Sci. USA 103, pp. 8459-8464 (2006).
Goff, et al., "Synthetic TLR4 and TLR7 ligands as influenza virus vaccine adjuvants induce rapid, sustained and broadly protective responses," J. Virol. 89, pp. 3221-3335 (2015).
Goubau, et al., "Antiviral immunity via RIG-I-mediated recognition of RNA bearing 5'-diphosphates," Nature 514, pp. 372-375 (2014).
Haronikova, et al., IFI16 Preferentially Binds to DNA with Quadruplex Structure and Enhances DNA Quadruplex Formation. PLoS One 11, pp. 1-19 (2016).
Hemmi, et al., "Small anti-viral compounds activate immune cells via the TLR7 MyD88-dependent signaling pathway," Nat. Immunol. 3, pp. 196-200 (2002).
Hornung, et al., "5'-triphosphate RNA is the ligand for RIG-I," Science 314, pp. 994-997 (2006).
Hornung, "Snapshot: Nucleic acid immune sensors, part 1," Immunity 41, pp. 868-868.e1 (2014).
Hou, et al., "MAVS forms functional prion-like aggregates to activate and propagate antiviral innate immune response," Cell 146, pp. 448-461 (2011).
Huen, et al., "Toll receptor agonist therapy of skin cancer and cutaneous T-cell lymphoma," Curr. Opin. Oncol. 26, pp. 237-244 (2014).
Jin, et al., "Structures of the HIN domain:DNA complexes reveal ligand binding and activation mechanisms of the AIM2 inflammasome and IFI16 receptor," Immunity. 36, 561-571 (2012).
Junt, et al., "Translating nucleic acid-sensing pathways into therapies," Nat Rev Immunol. 15, pp. 529-544 (2015).
Kato, et al., "Length-dependent recognition of double-stranded ribonucleic acids by retinoic acidinducible gene-I and melanoma differentiation-associated gene 5," J. Exp. Med. 205, 1601-1610 (2008).
Krieg, et al., "CpG motifs in bacterial DNA trigger direct B-cell activation," Nature 374, 546-549 (1995).
Li, et al., "Pivotal roles of cGAS-cGAMP signaling in antiviral defense and immune adjuvant effects," Science 341, pp. 1390-1394 (2013).
Li, et al., "Human cytomegalovirus tegument protein pUL83 inhibits IFI16-mediated DNA sensing for immune evasion," Cell Host Microbe 14, pp. 591-599 (2013).
Li, et al., "Acetylation modulates cellular distribution and DNA sensing ability of interferon-inducible protein IFI16," Proc. Natl. Acad. Sci. U.S.A., vol. 109, pp. 10558-10563 (2012).
Ohto, et al., "Structural basis of CpG and inhibitory DNA recognition by Toll-like receptor 9. Nature 520," pp. 702-705 (2015).
Orzalli, "Nuclear IFI16 induction of IRF-3 signaling during herpesviral infection and degradation of IFI16 by the viral ICP0 protein," Proc. Natl. Acad. Sci. U.S.A. 109, pp. E3008-E3017 (2012).
Pichlmair, et al., "Activation of MDA5 requires higher-order RNA structures generated during virus infection," J. Virol. 83, pp. 10761-10769 (2009).
Quintieri, et al., "Formation and Antitumor Activity of PNU-159682, A Major Metabolite of Nemorubicin in Human Liver Microsomes," Clin. Cancer Res. 11, pp. 1608-1617 (2005).
Sun, et al., "Cyclic GMP-AMP synthase is a cytosolic DNA sensor that activates the type I interferon pathway," Science 339, pp. 786-791 (2013).
Tanji, et al., "Toll-like receptor 8 senses degradation products of single-stranded RNA," Nat. Struct. Mol. Biol., vol. 22, pp. 109-115 (2015).
Temizoz, et al., "TLR9 and STING agonists synergistically induce innate and adaptive type II IFN," Eur. J. Immunol., vol. 45, pp. 1159-1169 (2015).
Thompson, et al., "Interferon gamma inducible protein (IFI) 16 transcriptionally regulates type I interferons and other interferon-stimulated genes and controls the interferon response to both DNA and RNA viruses," J Biol Chem. 289, pp. 23568-23581 (2014).
Unterholzner, et al., "IFI16 is an innate Immune sensor for intracellular DNA,". Nat Immunol. 11, pp. 997-1004 (2010).
Wu, et al., "Cyclic GMP-AMP is an endogenous second messenger in innate immune signaling by cytosolic DNA," Science 339, pp. 826-830 (2013).
International Preliminary Report on Patentability issued in International Patent Application No. PCT/IB2017/056131, dated Apr. 18, 2019.
MacDiarmid, et al., "Sequential Treatment of Drug-Resistant Tumors with Targeted Minicells containing siRNA or a Cytotoxic Drug," Nature Biotechnology, vol. 27, No. 7, pp. 643-651 (Jul. 2009).
Marjorie Robbins, et al., "siRNA and Innate Immunity," Ogligonucleoties, vol. 19, No. 2, pp. 89-102 (Jun. 2009).
Search Report issued in co-pending European Patent Application No. 17857944.7, dated Apr. 14, 2020.
Written Opinion issued in co-pending Singapore Patent Application No. 11201902940R, dated Jul. 15, 2020.
Mansoori B. et al., "Mechanisms of immune system activation in mammalians by small interfering RNA (siRNA)," Artif Cells Nanomed Biotechnol., vol. 44, No. 7, pp. 1589-1596 (Oct. 2015).
Notice of Reasons for Refusal issued in Japanese Patent Application No. 2019-518509, dated Oct. 19, 2021.
Tatematsu, et al., "Elucidating the RNA-Structure Recognized by Innate Immune Receptor TLR3," vol. 86(4), pp. 523-527 (Aug. 2014). (Abstract included).

\* cited by examiner

BACTERIAL MINICELLS FOR DELIVERING NUCLEIC ACID ADJUVANTS AND METHODS OF USING THE SAME

CROSS REFERENCE TO RELATED APPLICATIONS

This application claims priority from U.S. Provisional Patent Application No. 62/405,074, filed Oct. 6, 2016. The content of that application is incorporated herein by reference in its entirety.

FIELD OF INVENTION

The present disclosure relates generally to the field of nucleic acid-based therapy, and, in particular, to delivery of nucleic acid adjuvants to mammalian target cells (e.g., T cells, dendritic cells) using bacterially-derived, intact minicells. The disclosure has particular utility for treating cancer, especially in the context of promoting anti-tumor immune responses, and infections (e.g., viral infections).

BACKGROUND OF THE INVENTION

The following discussion is merely provided to aid the reader in understanding the disclosure and is not admitted to describe or constitute prior art thereto.

Recent advances have identified a number of nucleic acids that are sensed by receptors in mammalian cells. The engagement of nucleic acid receptors activates the innate immune system in multiple ways. For instance, the binding of certain nucleic acids (i.e., nucleic acid adjuvants) to cognate receptors results in triggering Type 1 and Type II interferons (IFNs). These interferons can function as adjuvants in augmenting anti-tumor activity by the immune system (reviewed in Junt and Barchet, 2015).

Aside from triggering cell-intrinsic and IFN-mediated effector mechanisms, nucleic acid sensor agonists can activate dendritic cells (DCs), promoting cytokine secretion, maturation and antigen presentation. This, in turn, enhances and shapes the quality of adaptive immune responses. Owing to their immune-enhancing properties, oligonucleotide or small-molecule agonists of nucleic acid sensors are being used in clinical trials to boost the immune response against poorly immunogenic cancers, and as adjuvants in therapeutic immunizations against cancer or in prophylactic vaccines against infections.

A number of agonists of nucleic acid sensors have been discovered and tested as adjuvants to provoke anti-viral immunity or enhance anti-tumor activity. Despite the promise of these agonists of nucleic acid sensors as adjuvants, few have actually entered clinical development.

This may be due to several factors. In particular, nucleic acid agonists need to be delivered into specific cells, such as dendritic cells, but these molecules do not have homing properties to assist in locating or entering the target cells. Additionally, when administered in vivo, free nucleic acids are unstable in serum and can be rapidly degraded by nucleases. As a result, nucleic acid adjuvants and agonists of nucleic acid sensors have been relegated to topical use, or must be covalently linked to protein antigens.

Thus, there is a clear need in the art for a delivery system capable of delivering therapeutic nucleic acid adjuvants and agonists of nucleic acid sensors to target cells. The present disclosure provides such a delivery system.

SUMMARY OF THE INVENTION

Described herein are compositions and methods for treating diseases using bacterially derived, intact minicells comprising nucleic acid adjuvants or agonists of nucleic acid sensors. In general, the disclosed minicell delivery vectors function by transporting the nucleic acid adjuvants or agonists of nucleic acid sensors to target cells, such as T cells or dendritic cells, to elicit an immune response to help fight various diseases, including cancer and/or infections.

In one aspect, the present disclosure provides compositions comprising (a) an intact minicell that comprising at least one nucleic acid adjuvant molecule, a plasmid comprising a segment that encodes at least one nucleic acid adjuvant molecule, or an agonist of a nucleic acid sensor, and (b) a pharmaceutically acceptable carrier therefore, wherein the at least one nucleic acid adjuvant molecule or agonist of a nucleic acid receptor triggers an immune response from a target cell.

In another aspect, the present disclosure provides methods of delivering a nucleic acid adjuvant or an agonist of a nucleic acid sensor to a target cell, comprising contacting a target cell with an intact minicell comprising (i) at least one nucleic acid adjuvant molecule, (ii) a plasmid comprised of a segment that encodes at least one nucleic acid adjuvant molecule, or (iii) at least one agonist of a nucleic acid sensor, wherein the target cell engulfs the minicell.

In yet another aspect, the present disclosure provides methods of treating a disease in a subject, comprising administering to a subject with a disease an intact minicell comprising (i) at least one nucleic acid adjuvant molecule, (ii) a plasmid comprising a segment that encodes at least one nucleic acid adjuvant molecule, or (iii) at least one agonist of a nucleic acid receptor, wherein the minicell is engulfed by a target cell following administration.

In some embodiments, the immune response produced in the target cells comprises the production of Type I interferon, including interferon-$\alpha$ and/or interferon-$\beta$.

In some embodiments, the at least one nucleic acid adjuvant comprises a nucleic acid that binds to at least one of TLR3, TLR7, TLR8, TLR9, RIG-I, MDA5, AIM2, cGAS, or IFI16.

In some embodiment, the intact minicell comprises at least two nucleic acid adjuvants. In other embodiments, the at least one nucleic acid adjuvant comprises a sequence of at least about 40 nucleotides, for example, the at least one nucleic acid adjuvant may be a 40-mer or a 50-mer double stranded RNA or DNA.

In some embodiments, the intact minicell comprises a nucleic acid adjuvant and an agonist of a nucleic acid sensor, and in some embodiments, the at least one agonist of a nucleic acid sensor comprises a polynucleotide product of PNPase1, poly(I:C), poly-ICLC, imiquimod, imidazoquioline resquimod, CpG-ODNs or 2'3' cyclic GAMP (GMP-AMP).

In some embodiments, the disclosed minicells may further comprise a bispecific ligand. In some embodiments, the bispecific ligand may comprise a first arm that carries specificity for a minicell surface structure and a second arm that carries specificity for a non-phagocytic mammalian cell surface receptor. For example, the minicell surface structure may be an O-polysaccharide component of a lipopolysaccharide on the minicell surface and the mammalian cell surface receptor may be capable of activating receptor-mediated endocytosis or macropinocytosis of the minicell. In some embodiments, the bispecific ligand comprises an antibody or antibody fragment.

In some embodiments, the composition comprises fewer than about 1 contaminating parent bacterial cell per $10^7$ minicells, per $10^8$ minicells, per $10^9$ minicells, per $10^{10}$ minicells, or per $10^{11}$ minicells.

In some embodiments, the plasmid encoding a nucleic acid adjuvant comprises a regulatory element operably linked to the segment that encodes at least one nucleic acid adjuvant, and in some embodiments, the plasmid encodes multiple nucleic acid adjuvant molecules.

In some embodiments, the target cell is a mammalian cell, such as a human immune cell.

For example, the target cell can be a monocytic cell, a macrophage, a T cell, or a dendritic cell or a NK cell or a iNKT cell. In some embodiments, the target cell is phagocytosis- or endocytosis- or macropinocytosis competent.

In some embodiments, the contact between the minicell and the mammalian cell can occur in vitro or in vivo.

In some embodiments, the disease being treated can be cancer or an infection.

In some embodiments, the administration of the disclosed minicell can further comprise administering a drug for the treatment of the disease to the subject, such as a chemotherapeutic or an anti-viral or an anti-bacterial. In these embodiments, the drug may be packaged in an intact minicell as well. In some embodiments, treatment may further comprise radiation treatment.

The invention further provides methods for loading killed bacterial cells with a drug. One such method involves creating a concentration gradient of the drug between an extracellular medium containing the killed bacterial cells and the killed bacterial cell cytoplasm. The drug naturally moves down this concentration gradient, into the killed bacterial cell cytoplasm. Leakage of the drug from the bacterial cytoplasm is prevented due to the bacterial cells being metabolically inactive.

Another method of loading killed bacterial cells with a drug involves culturing a bacterial cell under conditions, such that the bacterial cell transcribes and translates a therapeutic nucleic acid encoding the drug, such that the drug is released into the cytoplasm of the bacterial cell, and then killing the bacterial cell to form one or more killed bacterial cells containing the drug in their cytoplasm.

In accordance with another aspect, the present invention contemplates a method for formulating a killed bacterial cell with a plasmid-free functional nucleic acid. The method comprises co-incubating a plurality of killed bacterial cells with a functional nucleic acid in a buffer. In some embodiments, the co-incubation may involve gentle shaking, while in others the co-incubation is static. In some aspects, the co-incubation lasts about half an hour, while in others it lasts about an hour. In one embodiment, the buffer comprises buffered saline, for example, a 1× phosphate buffer solution. In another embodiment, the co-incubation is conducted at a temperature of about 4° C. to about 37° C., about 20° C. to about 30° C., about 25° C., or about 37° C. The co-incubation can comprise about $10^7$, $10^8$, $10^9$, $10^{10}$, $10^{11}$, $10^{12}$ or $10^{13}$ killed bacterial cells.

The foregoing general description and following detailed description are exemplary and explanatory and not limiting of the disclosure.

DETAILED DESCRIPTION

Figure 1:
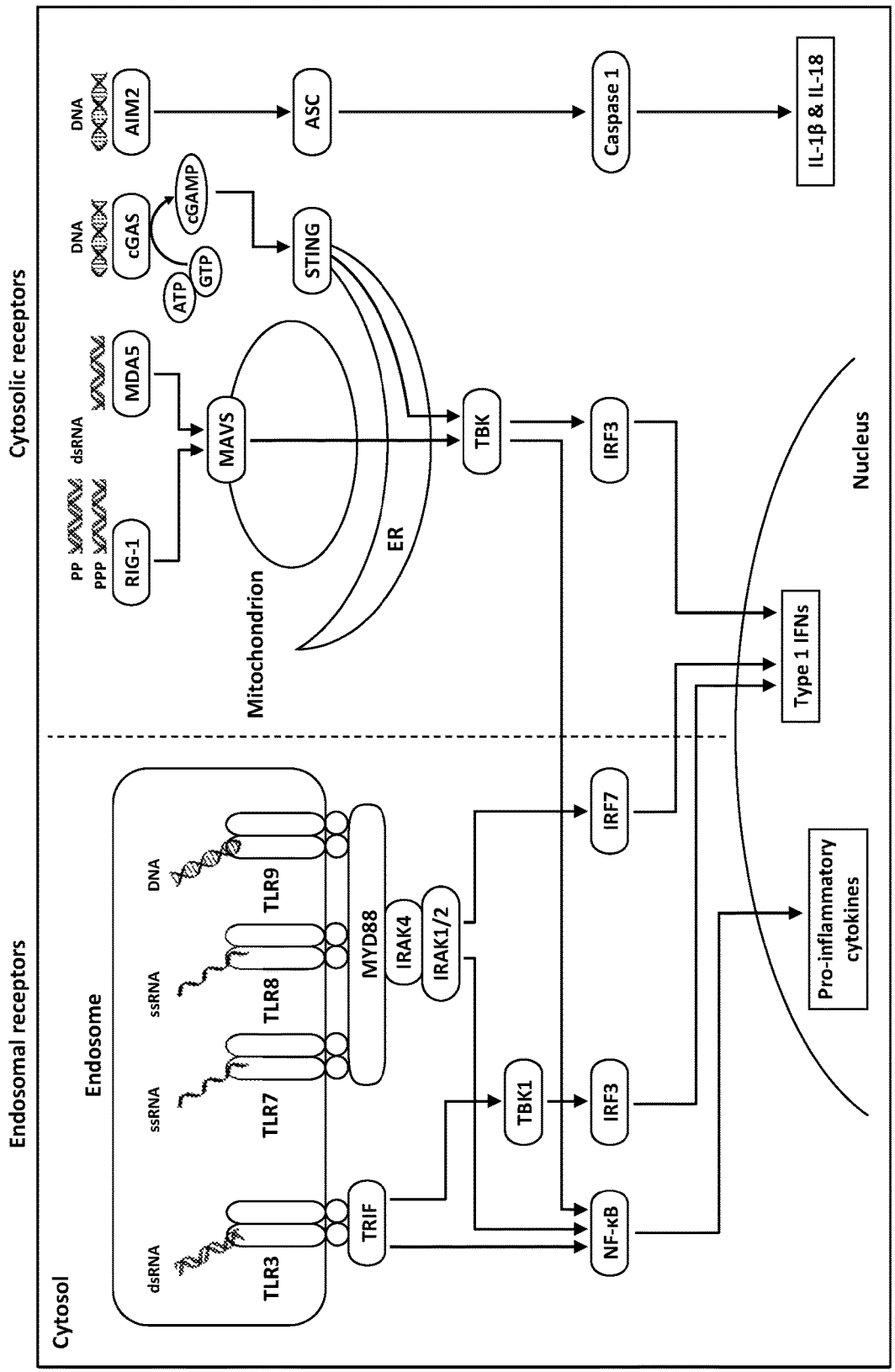
FIG. 1 shows endosomal and cytosolic nucleic acid-sensing pathways (adapted from Junt and Barchet, 2015). The figure indicates some of the major nucleic acid-sensing pathways described herein. Abbreviations include: cGAMP=cyclic GMP-AMP; cGAS=cGAMP synthase; DC=dendritic cell; dsRNA=double-stranded RNA; ER=endoplasmic reticulum; IL=interleukin; IRAK=IL-1 receptor-associated kinase; IRF=IFN-regulatory factor; MAVS=mitochondrial antiviral signaling protein; MDA5=melanoma differentiation-associated protein 5; MYD88=myeloid differentiation primary response protein 88; NF-κB=nuclear factor-κB; pDC=plasmacytoid DC; RIG-I=retinoic acid-inducible gene I; ssRNA=single-stranded RNA; STING=stimulator of IFN genes; TBK1=TANK-binding kinase 1; TRIF=TIR domain-containing adaptor protein inducing IFNβ; and XCR1=XC-chemokine receptor 1.
Figure 2:
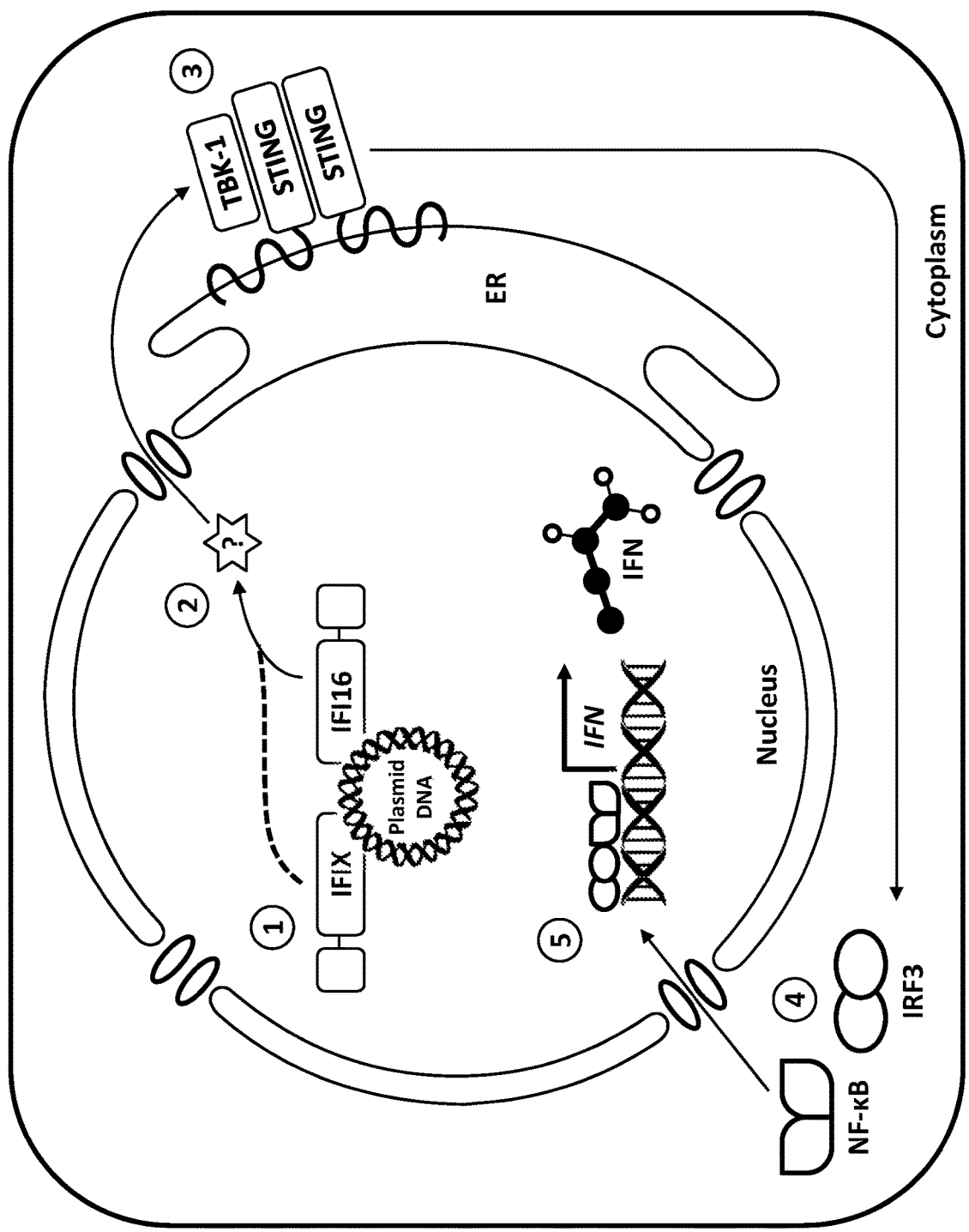
FIG. 2 shows a nucleic acid-sensing pathway in the nucleus (adapted from Diner, Lumm, and Christea, 2015). Following entry of double stranded foreign DNA into a host cell, it binds directly to DNA sensors IFI16 and IFIX (1). IFI16 signals to STING via a mechanism that has yet to be elucidated (2). Upon activation and dimerization of STING, TBK-1 is phosphorylated (3), resulting in the phosphorylation of IRF3 and NF-κB (4), which translocate back into the nucleus to induce the expression of cytokines (5).

The present disclosure provides novel minicell-based delivery vectors of nucleic acid adjuvants and/or agonists of nucleic acid sensors and methods of using the same. In particular, the disclosure has utility for enhancing a beneficial immune response to fight a disease in a patient, such as a neoplastic disease (e.g., cancer) or an infection. For example, the disclosed minicell delivery vectors can enhance anti-tumor efficacy when administering the disclosed minicell delivery vectors either alone or in combination with a bispecific ligand targeted, cytotoxic drug or siRNA or miRNA-packaged minicells in the same patient.

Previously, the present inventors discovered that therapeutically significant concentrations of siRNA or miRNA (~23 nucleotides in length) could be successfully packaged in intact minicells. This was unexpected because these molecules are large (~14,000 daltons) and it was not known that such large molecules could enter into intact minicells via the double outer membrane. Further, once packaged, these siRNAs or miRNAs did not leak or diffuse out from the minicells in vitro or in vivo.

The present inventors made and even more surprising discovery that much larger double stranded oligonucleotides that are 40 and 50 nucleotides long (40-mer and 50-mer) can be transported into the intact minicells and these oligonucleotides can also be packaged in therapeutically effective concentrations that do not diffuse out of the minicells. The present disclosure provides a detailed description of these minicells and methods of using the same.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

1. Therapeutic Minicell Compositions

The minicell compositions of the present disclosure are useful in delivering nucleic acid adjuvants to target cells in a mammal, in particular, a human cancer patient.

In the context of this disclosure, administering the disclosed minicell delivery vectors comprising nucleic acid adjuvants for treating a given disease (i.e., cancer) depends on several factors, in keeping with conventional medical practice. These factors include but are not limited to the patient's age, the status and progression of the disease, and whatever previous or current therapy the patient may have received or is receiving.

a. Minicells

As used herein, "minicell" refers to a derivative of a bacterial cell that is lacking in chromosomes ("chromosome-free") and is engendered by a disturbance in the coordination, during binary fission, of cell division with DNA segregation. Minicells are distinct from other small vesicles, such as so-called "membrane blebs" (~0.2 µm or less in size), which are generated and released spontaneously in certain situations but which are not due to specific genetic rearrangements or episomal gene expression. By the same token, intact minicells are distinct from bacterial ghosts, which are not generated due to specific genetic rearrangements or episomal gene expression. Bacterially derived minicells employed in this disclosure are fully intact and, thus, are distinguished from other chromosome-free forms of bacterial cellular derivatives characterized by an outer or defining membrane that is disrupted or degraded, even removed. See U.S. Pat. No. 7,183,105 at column 111, lines 54 et seq. The intact membrane that characterizes the minicells of the present disclosure allows retention of the therapeutic payload (e.g., nucleic acid adjuvants or agonists of nucleic acid sensors) within the minicell until the payload is released, post-uptake, within a target cell.

Minicells of the invention can be anucleate forms of *E. coli* or other bacterial cells (e.g., *S. typhimurium*). In *E. coli*, for example, mutation of min genes, such as minCD, can remove the inhibition of septum formation at the cell poles during cell division, resulting in production of a normal daughter cell and an anucleate minicell. See de Boer et al. (1992); Raskin & de Boer (1999); Hu & Lutkenhaus (1999); Harry (2001). For practicing the disclosed methods, in some embodiments it is desirable for minicells to have intact cell walls ("intact minicells").

In addition to min operon mutations, anucleate minicells may also be generated using a range of other genetic rearrangements or mutations that affect septum formation, for example in the divIVB1 in *B. subtilis*. See Reeve and Cornett (1975); Levin et al. (1992). Minicells also can be formed following a perturbation in the levels of gene expression of proteins involved in cell division/chromosome segregation. For example, overexpression of minE leads to polar division and production of minicells. Similarly, chromosome-less minicells may result from defects in chromosome segregation for example the smc mutation in *Bacillus subtilis* (Britton et al. (1998)), spoOJ deletion in *B. subtilis* (Ireton et al. (1994)), mukB mutation in *E. coli* (Hiraga et al. (1989)), and parC mutation in *E. coli* (Stewart and D'Ari (1992)). Gene products may be supplied in trans. When over-expressed from a high-copy number plasmid, for example, CafA may enhance the rate of cell division and/or inhibit chromosome partitioning after replication (Okada et al. (1994)), resulting in formation of chained cells and anucleate minicells (Wachi et al. (1989); Okada et al. (1993)).

Accordingly, minicells can be prepared for the present disclosure from any bacterial cell, be it of Gram-positive or Gram-negative origin. Furthermore, the minicells used in the disclosure may possess intact cell walls (i.e., are "intact minicells"), as noted above, and may be distinguished from other small vesicles, such as membrane blebs, which are not attributable to specific genetic rearrangements or episomal gene expression.

Thus, in some embodiments, the parental (source) bacteria can comprise one or more bacteria selected from Terra-/Glidobacteria (BV1), Proteobacteria (BV2), and BV4 including Spirochaetes, Sphingobacteria, and Planctobacteria. In some embodiments, the bacteria can comprise one or more selected from Firmicutes (BV3), such as Bacilli, Clostridia or Tenericutes/Mollicutes, or Actinobacteria (BV5) such as Actinomycetales or Bifidobacteriales.

In some embodiments, the bacteria can comprise one or more selected from Eobacteria (Chloroflexi, Deinococcus-Thermus), Cyanobacteria, Thermodesulfobacteria, thermophiles (Aquificae, Thermotogae), Alpha, Beta, Gamma (Enterobacteriaceae), Delta or Epsilon Proteobacteria, Spirochaetes, Fibrobacteres, Chlorobi/Bacteroidetes, Chlamydiae/Verrucomicrobia, Planctomycetes, Acidobacteria, Chrysiogenetes, Deferribacteres, Fusobacteria, Gemmatimonadetes, Nitrospirae, Synergistetes, Dictyoglomi, Lentisphaerae Bacillales, Bacillaceae, Listeriaceae, Staphylococcaceae, Lactobacillales, Enterococcaceae, Lactobacillaceae, Leuconostocaceae, Streptococcaceae, Clostridiales, Halanaerobiales, Thermoanaerobacterales, Mycoplasmatales, Entomoplasmatales, Anaeroplasmatales, Acholeplasmatales, Haloplasmatales, Actinomycineae, Actinomycetaceae, Corynebacterineae, Mycobacteriaceae, Nocardiaceae, Corynebacteriaceae, Frankineae, Frankiaceae, Micrococcineae, Brevibacteriaceae, and Bifidobacteriaceae.

For pharmaceutical use, a composition of the disclosure can comprise minicells that are isolated as thoroughly as possible from immunogenic components and other toxic contaminants. Methodology for purifying bacterially derived minicells to remove free endotoxin and parent bacterial cells are described in further detail below, as well as in WO 2004/113507, which is incorporated by reference here in its entirety.

Another structural element of a minicell derived from Gram-negative bacteria is the 0-polysaccharide component of lipopolysaccharide (LPS), which is embedded in the outer membrane via the lipid A anchor. This component is a chain of repeat carbohydrate-residue units, with as many as 70 to 100 repeat units of four to five sugars per chain. Because these chains are not rigid, in a liquid environment, as in vivo, they can adopt a waving, flexible structure.

As discussed in further detail below, minicells of the present disclosure can comprise at least one nucleic acid adjuvant or a plasmid that encodes a nucleic acid adjuvant for which delivery is desired, as well as at least one agonist of nucleic acid sensors. Nucleic acid adjuvants and agonists of nucleic acid sensors of the present disclosure can bind cognate receptors and produce a desired immune response (e.g., an IFN immune response). Both nucleic acid adjuvants and agonists of nucleic acid sensors of the present disclosure are discussed in more detail below.

Additionally, in some embodiments, the present disclosure provides methods of delivering at least one nucleic acid adjuvant or agonist of a nucleic acid sensor to a target cell, comprising contacting the target cell with an intact minicell comprising at least one nucleic acid adjuvant molecule, a plasmid comprising a segment that encodes at least one nucleic acid adjuvant molecule, or at least one agonist of a nucleic acid sensor, wherein the target cell engulfs the minicell. Following engulfment of the minicell by the target cell, the nucleic acid adjuvant molecule or agonist of a nucleic acid sensor is released into the cytoplasm of the target cell or expressed by the target cell. Minicells may be brought into contact with the target cells via bispecific ligands, as described in WO 2005/056749. Contact between the minicell and the target cell may be in vitro or in vivo.

b. Nucleic AcidAduvants

Contact between the bispecific ligands, killed bacterial cells and mammalian cells also may occur during one or more incubations in vitro. In one embodiment, the three elements are incubated together all at once. Alternatively, step-wise incubations may be performed. In one example of a step-wise approach, killed bacterial cells and bi-specific ligands are first incubated together to form bispecific ligand-targeted killed bacterial cells, which are then incubated with target cells. In another example, bispecific ligands are first incubated with target cells, followed by an incubation with killed bacterial cells. A combination of one or more in vitro incubations and in vivo administrations also may bring bispecific ligands, killed bacterial cells and mammalian target cells into contact.

Loading Killed Bacteria with Drugs

Preferably, killed bacterial cells of the invention contain a sufficient quantity of drug to exert the drug's physiological or pharmacological effect on a target cell. Also preferably, drugs contained within the killed bacterial cells are heterologous, or foreign, to the killed bacterial cells, meaning that the killed bacterial cells' parent bacterial cells do not normally produce the drug.

Both hydrophilic and hydrophobic drugs can be packaged in killed bacterial cells by creating a concentration gradient of the drug between an extracellular medium containing killed bacterial cells and the killed bacterial cell cytoplasm. When the extracellular medium contains a higher drug concentration than the killed bacterial cell cytoplasm, the drug naturally moves down this concentration gradient, into the killed bacterial cell cytoplasm. When the concentration gradient is reversed, however, the drug does not move out of the killed bacterial cells.

To load killed bacterial cells with drugs that normally are not water soluble, the drugs initially can be dissolved in an appropriate solvent. For example, Paclitaxel can be dissolved in a 1:1 blend of ethanol and cremophore EL (polyethoxylated castor oil), followed by a dilution in PBS to achieve a solution of Paclitaxel that is partly diluted in aqueous media and carries minimal amounts of the organic solvent to ensure that the drug remains in solution. Killed bacterial cells can be incubated in this final medium for drug loading. Thus, the inventors discovered that even hydrophobic drugs can diffuse into the cytoplasm of killed bacterial cells to achieve a high and therapeutically significant cytoplasmic drug load. This is unexpected because the killed bacterial cell membrane is composed of a hydrophobic phospholipid bilayer, which would be expected to prevent diffusion of hydrophobic molecules into the cytoplasm.

In some embodiments, the co-incubation may involve gentle shaking, while in others the co-incubation is static. A co-incubation of about one hour is sufficient, but shorter periods, such as about half an hour, also may be effective. In one embodiment, the buffer comprises buffered saline, for example a 1.times. phosphate buffer solution. The buffered saline can be in gelatin form. In another embodiment, the co-incubation is conducted at a temperature of about 4° C. to about 37° C.; about 20° C. to about 30° C.; about 25° C.; or about 37° C. In other aspects, the co-incubation can comprise about $10^7$, $10^8$, $10^9$, $10^{10}$, $10^{11}$, $10^{12}$ or $10^{13}$ killed bacterial cells. Specific parameters of temperature, time, buffer, minicell concentration, etc. can be optimized for a particular combination of conditions.

For the purposes of this disclosure, a "nucleic acid adjuvant" is a nucleic acid (i.e. polynucleotide or oligonucleotide) that binds to and/or activates a nucleic acid sensor or receptor (i.e. a cognate receptor) in a target cell and elicits a desirable immune response. A nucleic acid adjuvant may comprise DNA, RNA, and/or synthetic nucleotides. Further, a nucleic acid adjuvant may be single-stranded (ss) or double stranded (ds) and it may comprise more complex nucleic acid conformations such as hairpin loops, triplexes, and quadruplexes. For example, in some embodiments, the disclosed nucleic acid adjuvant may be ssDNA, dsDNA, ssRNA, or dsRNA.

Further, the nucleic acid adjuvant of the disclosure may be varying lengths. In particular, the nucleic acid may be very small, e.g., a dinucleotide. In other words, the nucleic acid adjuvant may be about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60 or more nucleotides in length.

Alternatively, the nucleic acid may have a size greater than about 27 nucleotides in length and up to about 4-about 5 KB in a single intact minicell. In some embodiments of the invention, the nucleic acid present in the bacterial minicell can be about 27, about 28, about 29, about 30, about 35, about 40, about 50, about 60, about 75, about 100, about 200, about 300, about 400, about 500, about 600, about 700, about 800, about 900, about 1000, about 1500, about 2000, about 2500, about 3000, about 3500, about 4000, about 4500, or about 5000 nucleotides in length.

Recent advances have identified a number of nucleic acids that are sensed by receptors in mammalian cells. The binding of these nucleic acids to cognate receptors results in triggering Type 1 and Type II interferons. These interferons can function as adjuvants in augmenting anti-tumor efficacy (reviewed in Junt and Barchet, 2015).

For example, nucleic acid sensors of the Toll-like receptor (TLR) family are confined to endosomes (Blasius and Beutler, 2010) and are selectively expressed by a few cell types, mainly those in the innate immune system (see FIG. 1). TLRs are transmembrane proteins consisting of amino-terminal leucine-rich repeats (LRRs) on the luminal side and a cytosolic Toll/IL-1R (TIR) domain.

In particular, TLR3 is activated by double-stranded RNA (dsRNA). TLR7 detects single-stranded RNA (ssRNA) and short dsRNA. TLR8 binds short ssRNA and ssRNA breakdown products (Tanji et al. (2015)). TLR9 instead senses DNA that contains unmethylated CpG motifs that are commonly found in bacterial DNA (Ohto et al. (2015)).

In TLR7, TLR8 and TLR9, the TIR domain initiates signaling by aggregating the adaptor protein myeloid differentiation primary response protein 88 (MYD88). Activation of the MYD88-dependent signaling cascade ultimately leads to the activation of nuclear factor-κB (NF-κB) and the transcription of genes encoding pro-inflammatory cytokines.

Exclusively in plasmacytoid dendritic cells (pDCs), the MYD88 signaling complex is able to induce ample transcription of genes encoding various interferon-α (IFNα) subtypes via a direct activation of IFN-regulatory factor 7 (IRF7).

By contrast, TLR3 signals via TIR domain-containing adaptor protein inducing IFNβ (TRIF), which activates NF-κB, mitogen activated protein kinase (MAPK) and IRF3 signaling and results in the transcription of IFNB and pro-inflammatory cytokines (Hornung (2014)).

Thus, in some embodiments, the nucleic acid adjuvants of the disclosure may bind to and activate TLR7, TLR8, and/or TLR9. The nucleic acid adjuvants may bind to and activate these receptors in various cell types, including immune cells and non-immune cells. For instance, in some embodiments, the nucleic acid adjuvants may be targeted to immune cells such as T cells and/or monocytic cells, which can include but are not limited to, monocytes, macrophages, dendritic cells (e.g., pDCs, conventional dendritic cells, or myeloid dendritic cells).

In some embodiments, the nucleic acid adjuvants of the disclosure may bind to and activate TLR3. In these embodiments, the nucleic acid adjuvants may also be targeted to immune cells or non-immune cells.

Another set of RNA and DNA sensors that may be activated by the disclosed nucleic acid adjuvants is broadly expressed in the cytosol of immune and non-immune cells (see FIG. 1). The DExD/H-box helicases retinoic acid-inducible gene I (RIG-I) and melanoma differentiation-associated protein 5 (MDA5) detect complementary dsRNA structures. Both RIG-I and MDA5 consist of a carboxy-terminal ligand-binding domain, a central DEAxD/H-box helicase domain and an N-terminal caspase activation and recruitment domain (CARD). These CARDs engage similar CARDs of the signalling adaptor mitochondrial antiviral signalling protein (MAVS) on the outer mitochondrial membrane, which leads to multimerization of MAVS and activation of the MAVS signalling complex (Hou et al. (2011)).

RIG-I is activated by 5' triphosphorylated or 5' diphosphorylated ends of short dsRNA (Hornung et al. (2006); Goubau et al. (2014)). MDA5 is thought to bind dsRNA and branched high-molecular RNA forms (Kato et al. (2008); Pichlmair et al. (2009)).

Thus, in some embodiments, the nucleic acid adjuvants of the disclosure may bind to and activate RIG-I and/or MDA5. In these embodiments, the nucleic acid adjuvants may also be targeted to immune cells or non-immune cells.

Another cytosolic sensor that may be activated by the disclosed nucleic acid adjuvants is cyclic GMP-AMP (cGAMP) synthase (cGAS) (Sun et al. (2013)), a receptor for dsDNA. Upon ligand binding, cGAS produces the non-canonically linked cyclic dinucleotide (CDN) [G(2',5')pA (3',5')p] (2'3'-cGAMP), which functions as a second messenger to activate the stimulator of IFN genes (STING) on the endoplasmic reticulum (ER) (Wu et al. (2013); Gao et al. (2013)).

Thus, in some embodiments, the nucleic acid adjuvants of the disclosure may bind to and activate cGAS. In these embodiments, the nucleic acid adjuvants may also be targeted to immune cells or non-immune cells.

By contrast, absent in melanoma 2 (AIM2), which is another cytosolic receptor for dsDNA that may be activated by the disclosed nucleic acid adjuvants, triggers the release not of IFNs but of IL-1β and IL-18.

Thus, in some embodiments, the nucleic acid adjuvants of the disclosure may bind to and activate AIM2. In these embodiments, the nucleic acid adjuvants may also be targeted to immune cells or non-immune cells.

Recent studies have established the existence of cellular DNA sensors that detect dsDNA within the nucleus to trigger immune signalling. Although the actions of these DNA sensors have been predominantly studied in the cytosol and endosomes, emerging evidence is shifting focus to the nucleus.

IFI16 (interferon-inducible protein 16) is a DNA sensor (Dawson and Trapani (1995)) that belongs to the highly homologous HIN-200 (hemopoietic expression-interferon-inducibility-nuclear localization) protein family characterized by a 200 amino acid motif containing a DNA binding domain at the C-terminus and a PYRIN domain at the N-terminus, involved mainly in protein-protein interactions. IFI16 is the first viral DNA sensor shown to function within the nucleus and also in the cytoplasm (Dawson and Trapani (1995); Unterholzner et al. (2010)). IFI16 subcellular localization is influenced by the cell type, post-translational modification and cell treatment.

For example, pathogen invasion causes the formation of IFI16 foci in the cytoplasm and induces interferon β (IFNB) gene expression (Unterholzner et al. (2010)) and UV-light causes the transfer of IFI16 from the nucleus to the cytoplasm (Costa et al. (2011)).

The DNA sensing ability of IFI16 is related to the activation of interferon 3 expression through interaction with stimulator of interferon genes (Unterholzner et al. (2010)), and interferon α expression (Thompson et al. (2014)). IFI16 binding to DNA is not sequence-specific or AT content-dependent, but is strongly DNA length-dependent (Unterholzner et al. (2010)).

Based on crystallographic studies, the IFI16 HIN-B—double stranded DNA interface is accomplished through electrostatic interactions between the negatively charged sugar-phosphate backbone and positively charged protein residues (Jin et al. (2012)). IFI16 binding to long plasmid DNA was studied and preferences for supercoiled over linear forms and for cruciform structure over double stranded DNA was observed (Brazda et al. (2012)).

IFI16 shows preferential binding to quadruplex DNA with positive effects on quadruplex DNA formation and stabilization (Haronikova et al. (2016)). Across non-immune cell types, IFI16 predominantly localizes to the nucleus (Diner et al. (2015); Li et al. (2012), (2013); Orzalli et al. (2012)).

Thus, in some embodiments, the nucleic acid adjuvants of the disclosure may bind to and activate IFI16. In these embodiments, the nucleic acid adjuvants may also be targeted to immune cells or non-immune cells.

In addition to those mentioned above, several other nucleic acid sensors have been described in the art. The skilled artisan will understand that any known nucleic acid sensor may be activated or targeted using the disclosed minicell delivery vectors comprising a nucleic acid adjuvant designed to bind to the cognate receptor (i.e. nucleic acid sensor). Accordingly, the nucleic acid sensors that may be targeted or activated by the disclosed compositions are not particularly limited.

For the purposes of this disclosure, in some embodiments, the minicell delivery vectors may comprise at least one nucleic acid adjuvant. For example, the minicell delivery vector may comprise at least 1, at least 2, at least 3, at least 4, at least 5, at least 6, at least, 7, at least 8, at least 9, or at least 10 different nucleic acid adjuvants. In some embodiments, the disclosed minicell delivery vector may comprise both at least one nucleic acid adjuvant and at least one agonist of a nucleic acid sensor.

c. Nucleic Acid-Sensing Pathway Agonists

For the purposes of this disclosure, an "agonist of a nucleic acid sensor" is a compound-either natural or synthetic—that is capable of agonizing known nucleic acid sensors, including but not limited to those disclosed in the previous section, and can be used to elicit a desired immune response (i.e. an IFN response).

For example, polynucleotide products of the enzyme polynucleotide phosphorylase (PNPase 1) have been studied as synthetic inducers of IFN activity (Field et al. (1967)). Similarly, the dsRNA mimetic polyinosinic:polycytidylic acid (poly(I:C)), was shown to function as an agonist for both TLR3 and MDA5 (Alexopoulou et al. (2001); Gitlin et al. (2006)).

An analogue of poly(I:C), poly-ICLC, that is formulated with poly-1-lysine to increase RNase resistance, is currently being evaluated as a promising cancer vaccine adjuvant (reviewed in Ammi et al. (2014)).

Small molecule agonists of nucleic acid sensors have also been developed. As an example, imiquimod, an imidazoquinoline derivative, is an agonist of TLR7 (Hemmi et al. (2002)). It has been shown to be effective in the treatment of dermatological neoplasias, such as basal cell carcinoma and actinic keratosis. Local induction of pro-inflammatory cytokines, local recruitment of immune cells, and improved antigen presentation for the induction of T helper 1 ($T_H1$) and $CD8^+$ T cell responses, all of which result from administration of imiquimod, are considered to be important for treatment success.

Agonists may also be able to bind to two or more nucleic acid sensors. For example, imidazoquinoline resiquimod is a dual agonist of TLR7 and TLR8. In humans, resiquimod therefore potently activates additional cell types and elicits a broader range of cytokines. A drawback may be that this probably contributes to the more frequent occurrence of systemic adverse effects observed in clinical trials (Huen and Rook (2014)).

Attempts are being made to develop agonists for human STING and these are being modelled on the physiological agonist 2'3'-cGAMP, which has recently been shown to have vaccine adjuvant properties (Li et al. (2013)).

Synthetic oligonucleotides can also be designed and used as agonists of nucleic acid sensors. For example, TLR9-stimulatory synthetic CpG oligodeoxynucleotides (CpG-ODNs) were designed based on the immune-stimulatory properties of bacterial DNA that, in contrast to human DNA, is rich in unmethylated CpG motifs (Krieg at al. (1995). Optimization of sequence features and backbone modifications led to CpG-ODN subtypes that preferentially activate either B cells or pDCs. Multiple clinical trials are under way to determine antitumour activity of CpG-ODNs, in combination with chemotherapy or in therapeutic vaccines.

The combined use of different agonists may prove more beneficial, as recent data have indicated that co-engagement of multiple nucleic acid receptors elicited the most potent immune responses in preclinical trials of vaccine adjuvants (Goff et al. (2015); Temizoz et al. (2015)).

Thus, in some embodiments, the minicell delivery vectors may comprise at least one agonist of a nucleic acid sensor. For example, the minicell delivery vector may comprise at least 1, at least 2, at least 3, at least 4, at least 5, at least 6, at least, 7, at least 8, at least 9, or at least 10 different agonists of nucleic acid sensors. In some embodiments, the disclosed minicell delivery vector may comprise both at least one nucleic acid adjuvant and at least one agonist of a nucleic acid sensor.

d. Nucleic Acids Encoding Nucleic Acid Adjuvants

In some embodiments of the present disclosure, the disclosed minicell delivery vectors can comprise nucleic acids that encode at least one nucleic acid adjuvant. For example, a plasmid may encode a nucleic acid adjuvant that is expressed inside of a target cell (i.e. a mammalian cell or an immune cell). This makes possible endogenous delivery of nucleic acid adjuvants, which, for the treatment of some diseases, may be advantageous over the transient nature of exogenous delivery.

Thus, bacterially-derived intact minicells may carry plasmid DNA encoding one or more nucleic acid adjuvants, including but not limited to, double-stranded or single-stranded RNA or DNA that can bind to and/or activate TLR3, TLR7, TLR8, TLR9, RIG-I, MDA5, AIM2, cGAS, or IFI16. Using minicells that encode multiple nucleic acid adjuvants, it is possible to produce a robust immune response in a patient. For example, a first nucleic acid adjuvant can be expressed from an U6 promoter and a second nucleic acid adjuvant can be expressed from an H1 promoter. These multiple expression cassettes may be are carried on a single plasmid, but may also be on different plasmids.

In some embodiments, different nucleic acid adjuvants can be expressed from a single promoter, where the recombinant plasmid carries an expression cassette comprised of multiple nucleic acid adjuvant sequences, which are linked together via non-coding polynucleotide sequences. A single gene transcription terminator can be placed downstream of the complete expression cassette.

In some embodiments, a plasmid may encode the sense and antisense strands of an dsRNA or dsDNA as two independent transcripts that, after expression within a target cell, hybridize to form a functional nucleic acid adjuvant. In some embodiments, a plasmid encodes one or more dsRNA or dsDNA that each are expressed as a single transcript that forms a short hairpin stem-loop structure. The hairpin structure may be processed by other enzymes in the cell to produce a functional nucleic acid adjuvant.

A nucleic acid encoding a nucleic acid adjuvant molecule to be introduced via the approach described in this section also can have the desired coding segment linked operatively to a regulatory element, such as a promoter, a terminator, an enhancer and/or a signal sequence. A suitable promoter can be tissue-specific or even cell-specific, as the therapeutic context dictates.

A signal sequence can be used, for the purposed of this disclosure, to effect secretion of an expression product or localization of an expression product to a particular cellular compartment. Thus, a nucleic acid (i.e. a plasmid) encoding a therapeutic nucleic acid adjuvant molecule that is delivered via intact minicells may include a signal sequence, in proper reading frame, such that the expression product of interest is secreted by an engulfing cell or its progeny, thereby to influence surrounding cells, in keeping with the chosen treatment paradigm. Illustrative signal sequences include the haemolysin C-terminal secretion sequence, described in U.S. Pat. No. 5,143,830, the BAR1 secretion sequence, disclosed in U.S. Pat. No. 5,037,743, and the signal sequence portion of the zsig32 polypeptide, described in U.S. Pat. No. 6,025,197.

e. Reporter Elements

A nucleic acid adjuvant molecule or an agonist of a nucleic acid sensor delivered via the disclosed minicell delivery vectors may further comprise a reporter element. A reporter element confers on its target host cell a readily detectable phenotype or characteristic, typically by encoding a polypeptide, not otherwise produced by the host, that can be detected, upon expression, by histological or in situ analysis, such as by in vivo imaging techniques. For example, a reporter element delivered by an intact minicell, according to the present disclosure, could code for a protein that produces, in the engulfing host cell, a colorimetric or fluorometric change that is detectable by in situ analysis and that is a quantitative or semi-quantitative function of transcriptional activation. Illustrative of these proteins are esterases, phosphatases, proteases and other enzymes, the activity of which generates a detectable chromophore or fluorophore.

Preferred examples of reporter elements include, but are not limited to, *E. coli* 3-galactosidase, which effects a color change via cleavage of an indigogenic substrate, indolyl-3-D-galactoside, and a luciferase, which oxidizes a long-chain aldehyde (bacterial luciferase) or a heterocyclic carboxylic acid (luciferin), with the concomitant release of light. Also useful in this context is a reporter element that encodes the green fluorescent protein (GFP) of the jellyfish, *Aequorea victoria*, as described by Prasher et al. (1995). The field of GFP-related technology is illustrated by two published PCT applications, WO 95/21191 (discloses a polynucleotide sequence encoding a 238 amino-acid GFP apoprotein, containing a chromophore formed from amino acids 65 through 67) and WO 95/21191 (discloses a modification of the cDNA for the apopeptide of *A. victoria* GFP, providing a peptide having altered fluorescent properties), and by a report of Heim et al. (1994) of a mutant GFP, characterized by a 4-to-6-fold improvement in excitation amplitude.

Other genes for use as a reporter element include those that can transform a target cell of the minicell delivery vector to express distinguishing cell-surface antigens, e.g., viral envelope proteins such as HIV gp120 or herpes gD, which are readily detectable by immunoassays.

f. Packaging Nucleic Acid Adjuvants in Minicells

Nucleic acid adjuvants that can be encoded by a nucleic acid can be introduced into minicells by transforming the encoding nucleic acid into the parental bacterial cell in a vector, such as a plasmid, that encodes the nucleic acid adjuvant. When a minicell is formed from the parental bacterial cell, the minicell retains certain copies of the plasmid and/or the expression product, the nucleic acid adjuvant. More details of packaging an expression product into a minicell is provided in WO 03/033519, the content of which is incorporated into the present disclosure in its entirety by reference.

Nucleic acid adjuvants also can be packaged into minicells directly. Thus, a nucleic acid adjuvant can be packaged directly into intact minicells by co-incubating a plurality of intact minicells with the nucleic acid adjuvant in a buffer. The buffer composition can be varied, as a function of conditions well known in this field, to optimize the loading of the nucleic acid adjuvant into the intact minicells. The buffer also may be varied in dependence on the nucleotide sequence and the length of the nucleic acid adjuvant to be loaded in the minicells. Once packaged, the nucleic acid remains inside the minicell and is protected from degradation. Prolonged incubation studies with siRNA-packaged minicells incubated in sterile saline showed, for example, no leakage of siRNAs.

In some embodiments, multiple nucleic acid adjuvants can be packaged in the same minicell. Such an approach can be used to produce a robust immune response in a patient. For example, cancer patients routinely present with tumors capable of evading the innate immune response. To combat this evasion, minicells can be packaged with therapeutically significant concentrations of nucleic acid adjuvants or agonists of nucleic acid sensors to immune cells (e.g., T cells, dendritic cells, or monocytes) to stimulate the immune system to detect and destroy the cancer cells. Furthermore, packaging into the same minicell multiple nucleic acid adjuvants or agonists of nucleic acid sensors can enhance therapeutic success since many cognate receptors belong to distinct signaling pathways and can induce the production and secretion of various cytokines or chemokines including IFNα or IFNβ. More details of directly packaging a nucleic acid into a minicell is provided in WO 2009/027830, the contents of which are incorporated into the present disclosure in its entirety by reference.

Small molecule drugs, including agonists of nucleic acid sensors, whether hydrophilic or hydrophobic, can be packaged in minicells by creating a concentration gradient of the drug between an extracellular medium containing minicells and the minicell cytoplasm. When the extracellular medium contains a higher drug concentration than the minicell cytoplasm, the drug naturally moves down this concentration gradient, into the minicell cytoplasm. When the concentration gradient is reversed, however, the drug does not move out of the minicells.

g. Directing Minicells to Target Cells

For the purposes of this disclosure, the minicells of a composition, as described above, are directed to a target cell via a ligand. Target cells may include mammalian cells, and, in particular, human cells. Target cells may be immune cells or non-immune cells, but in preferred embodiments, the target cells are immune cells, such as T cell, monocytes, dendritic cells, and/or macrophages.

In some embodiments the ligand is "bispecific." That is, the ligand displays a specificity for both minicell and target (e.g., immune) cell components, such that it causes a given minicell to bind to the target cell, whereby the latter engulfs the former. Use of bispecific ligands to target a minicell to a tumor cell is further described in WO 05/056749 and WO 05/079854, the respective contents of which are incorporated here in the entirety by reference. Once such a ligand is attached to a minicell, the unoccupied specificity ("monospecificity") of the ligand pertains until it interacts with the target cell.

The ligand can be expressed from within the minicells or their parents and then is displayed on the minicells surface. Alternatively, the ligand can be attached to ("coated on") the cell membrane of the minicells, e.g., by virtue of ligand-receptor interaction. In either instance the ligand does not require a specificity to the minicell and only displays a specificity to a component that is characteristic of the target cells. That is, such component need not be unique to the target cells, per se, or even to the particular kind of immune cell being targeted, so long as the target cells present the component on their cell surface.

In some embodiments, minicell delivery vectors contained in an administered composition of the disclosure, may contact and bind to a targeted type of cell, eliciting their uptake into the cells, which then are affected by the therapeutic payload. That payload can be at least one nucleic acid adjuvant and/or at least one agonist of a nucleic acid sensor.

The inventors found that this targeted delivery approach is broadly applicable to a range of mammalian target cells, including cells that normally are refractory to specific adhesion and endocytosis of minicells. Thus, the type of cell being targeted is not particularly limited. Indeed, the binding of a minicell to a target cell precedes rapid endocytosis of the minicells by even non-phagocytic cells. However, in some embodiments, a suitable target cell for the present disclosure is characterized by expression of a cell surface receptor that, upon binding of a ligand, facilitates endocytosis or macropinocytosis.

The term "endocytosis" encompasses (1) phagocytosis and (2) pinocytosis, itself a category inclusive of (2a) macropinocytosis, all of which tend to access the late-endosome/lysosome pathway. The interaction between the ligand on a minicell and a mammalian cell surface receptor, the present inventors discovered, activates a particular endocytosis pathway, involving receptor mediated endocytosis (rME) to the late-endosomal/lysosomal compartment. By virtue of such an endocytosis pathway, the present inventors further discovered that the minicells were able to release their payload into the cytoplasm of the target mammalian cell. In the event the payload is an encoding nucleic acid, the nucleic acid not only is not completely degraded in the late-endosomal/lysosomal compartment, but also is expressed in the target mammalian cell.

Ligands useful in the above-described targeted delivery approach, pursuant to this disclosure, include any agent that binds to a surface component on a target cell and to a surface component on a minicell. In some embodiments, the surface component on a target cell is a receptor. The ligands can comprise a polypeptide and/or carbohydrate component. In some embodiments, antibodies are preferred ligands.

For example, an antibody that carries specificity for a surface component, such as an immune cell marker, on the target mammalian cells can be used efficiently to target the minicells to the target cells to produce an immune response.

In some embodiments, preferred ligands comprise antibodies and/or antibody derivatives. In its present use, the term "antibody" encompasses an immunoglobulin molecule obtained by in vitro or in vivo generation of an immunogenic response. Accordingly, the "antibody" category includes monoclonal antibodies and humanized antibodies, as well as antibody derivatives, such as single-chain antibody fragments (scFv), bispecific antibodies, etc. A large number of different bispecific protein and antibody-based ligands are known, as evidenced by the review article of Caravella and Lugovskoy (2010), incorporated here by reference in its entirety. Antibodies and antibody derivatives useful in the present disclosure also can be obtained by recombinant DNA techniques.

This disclosure provides a composition comprising bispecific ligand targeted, nucleic acid adjuvant and/or agonist of nucleic acid receptor-packaged minicells that are able to deliver therapeutically significant concentrations of the nucleic acid adjuvant or agonist of a nucleic acid receptor into desired cells of the mammalian host such that a desired, beneficial immune response is elicited in the host.

2. Methods of Treatment

Provided herein are methods of treating or preventing various diseases or conditions with the disclosed minicell delivery vectors. In some embodiments, the disease to be treated or prevented comprises a tumor, cancer, malignant disease, or cancer cell proliferation. In some embodiments, the disease to be treated or prevented is an infection, such as a viral infection. More specifically, the disclosure provides for methods of activating an IFN immune response, and, in particular, the production of interferon type 1. Such methods may comprise administering a therapeutically effective amount of the disclosed minicell delivery vectors containing at least one nucleic acid adjuvant and/or at least one agonist of a nucleic acid sensor.

The disclosed methods may be used to stimulate the immune system to recognize and/or destroy foreign bodies or pathogen cells (i.e. viruses, cells infected with viruses, cancer cells, etc.) by administering intact minicells that contain at least one nucleic acid adjuvant, a nucleic acid encoding at least one nucleic acid adjuvant, or an agonist of a nucleic acid sensor.

In some embodiments, administration of the disclosed minicells containing a nucleic acid adjuvant or an agonist of a nucleic acid sensor is not intended to directly kill a foreign body or pathogenic cell. Rather, the administration of such minicells is intended to adjuvate the therapeutic efficacy of another therapeutic agent.

For instance, in some embodiments, a subject may be administered a first dose of the disclosed minicells containing a nucleic acid adjuvant or an agonist of a nucleic acid sensor and a second dose of a minicell containing another therapeutic agent (i.e. siRNA or another biologic compound) or drug. In some embodiments, the second dose may comprise a cytotoxic drug, such as a chemotherapeutic, and in some embodiments, the first and second doses may be targeted to different cell types. For instance, a minicell for use in the first dose containing a nucleic acid adjuvant or an agonist of a nucleic acid sensor may be targeted to an immune cell, while a minicell for use in the second dose containing a chemotherapeutic drug may be targeted to a tumor cell. Chemotherapeutics and drugs that are co-administered or administered before or after administration of the disclosed minicells comprising a nucleic acid adjuvant or an agonist of a nucleic acid sensor may be packaged in another minicell or another type of targeted particle, or the chemotherapeutics or drugs may be administered in an unencapsulated, free form.

Additionally, the disclosed minicells comprising a nucleic acid adjuvant or an agonist of a nucleic acid sensor may be administered to a subject that is receiving, has received, or will received radiation therapy for the treatment of cancer. Indeed, the disclosed minicells comprising a nucleic acid adjuvant or an agonist of a nucleic acid sensor can augment any known form of cancer treatment by, for example, increasing a subject's innate anti-tumor immune defense.

Indeed, the disclosed methods allow for the administration of oligonucleotides that are greater than about 27 nucleotides in length and up to about 4-about 5 KB in a single intact minicell. In other embodiments, the nucleic acid can be very small, with a size of at least about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60 or more nucleotides in length.

These oligonucleotides can trigger immunomodulation in the form of production of Type I interferon (IFNα and IFNβ). Production of Type I interferon has been shown to produce an adjuvant effect and assist in treating cancer and/or infections. Thus, in some embodiments, administering the disclosed minicells containing a nucleic acid adjuvant or an agonist of a nucleic acid sensor in connection with another therapeutic agent or drug will result in higher antitumor efficacy than administering the other therapeutic agent or drug alone.

The disclosed methods are a dramatic improvement over the prior art, as it is known to be difficult to administer Type I interferons directly. Interferons have a short half-life in circulation and IV administration of interferons generally results in severe side effects. Thus, the disclosed methods provide a novel means of promoting the production of a therapeutically effective level of interferons in a manner that is physiologically acceptable.

The disclosed minicells may be targeted directly to specific immune cells, or they may be non-targeted. In some embodiments, non-targeted intact minicells are phagocytosed in macrophages or other monocytic cells, and thereby elicit the desired immunmodulation in these cells.

Without being bound by theory, it is believed that the disclosed methods work by activating interferon type 1 production, which in turn acts to stimulate immune cells that are capable of killing cancer cells or infected cells. It is known that the immune system is often suppressed in cancer patient, and the disclosed methods may provide a means of "waking up" the cancer patient's immune system.

Thus, once the cancer patient's immune system is active, the success of cytotoxic frontline therapies will be more efficacious. Pairing the disclosed minicells containing a nucleic acid adjuvant or an agonist of a nucleic acid sensor with intact minicells comprising a cytotoxic drug provides superior efficacy over the treatment of the drug alone, as shown in Examples 1 and 2.

As discussed in more detail below, formulations of the invention can be administered via various routes and to various sites in a mammalian body, to achieve the therapeutic effect(s) desired, either locally or systemically. Delivery may be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The mode and site of administration is dependent on the location of the target cells.

a. Purity

Minicells of the invention are substantially free from contaminating parent bacterial cells. Thus, minicell-containing formulations of the invention preferably contain fewer than about 1 contaminating parent bacterial cell per $10^7$ minicells, more preferably contain fewer than about 1 contaminating parent bacterial cell per $10^8$ minicells, even more preferably contain fewer than about 1 contaminating parent bacterial cell per $10^9$ minicells, still more preferably contain fewer than about 1 contaminating parent bacterial cell per $10^{10}$ minicells and most preferably contain fewer than about 1 contaminating parent bacterial cell per $10^{11}$ minicells.

Methods of purifying minicells are known in the art and described in PCT/IB02/04632, WO 2004/113507, and U.S. Pat. No. 8,591,862. One such method combines cross-flow filtration (feed flow is parallel to a membrane surface; Forbes, 1987) and dead-end filtration (feed flow is perpendicular to the membrane surface). Optionally, the filtration combination can be preceded by a differential centrifugation, at low centrifugal force, to remove some portion of the bacterial cells and thereby enrich the supernatant for minicells.

Another purification method employs density gradient centrifugation in a biologically compatible medium. After centrifugation, a minicell band is collected from the gradient, and, optionally, the minicells are subjected to further rounds of density gradient centrifugation to maximize purity. The method may further include a preliminary step of performing differential centrifugation on the minicell-containing sample. When performed at low centrifugal force, differential centrifugation will remove some portion of parent bacterial cells, thereby enriching the supernatant for minicells.

Particularly effective purification methods exploit bacterial filamentation to increase minicell purity. Thus a minicell purification method can include the steps of (a) subjecting a sample containing minicells to a condition that induces parent bacterial cells to adopt a filamentous form, followed by (b) filtering the sample to obtain a purified minicell preparation.

Known minicell purification methods also can be combined. For example, one highly effective combination of methods is as follows:

Step A: Differential centrifugation of a minicell producing bacterial cell culture. This step, which may be performed at 2000 g for about 20 minutes, removes most parent bacterial cells, while leaving minicells in the supernatant.

Step B: Density gradient centrifugation using an isotonic and non-toxic density gradient medium. This step separates minicells from many contaminants, including parent bacterial cells, with minimal loss of minicells. Preferably, this step is repeated within a purification method.

Step C: Cross-flow filtration through a 0.45 μm filter to further reduce parent bacterial cell contamination.

Step D: Stress-induced filamentation of residual parent bacterial cells. This may be accomplished by subjecting the minicell suspension to any of several stress-inducing environmental conditions.

Step E: Antibiotic treatment to kill parent bacterial cells.

Step F: Cross-flow filtration to remove small contaminants, such as membrane blebs, membrane fragments, bacterial debris, nucleic acids, media components and so forth, and to concentrate the minicells. A 0.2 m filter may be employed to separate minicells from small contaminants, and a 0.1 m filter may be employed to concentrate minicells.

Step G: Dead-end filtration to eliminate filamentous dead bacterial cells. A 0.45 um filter may be employed for this step.

Step H: Removal of endotoxin from the minicell preparation. Anti-Lipid A coated magnetic beads may be employed for this step.

In some embodiments, the purification process achieves removal of (a) smaller vesicles, such as membrane blebs, which are generally smaller than about 0.2 m in size, (b) free endotoxins released from cell membranes, and (c) parental bacteria, whether live or dead, and their debris, which are sources of free endotoxins, too. Such removal can be implemented with, inter alia, a 0.2 μm filter to remove smaller vesicles and cell debris, a 0.45 μm filter to remove parental cells following induction of the parental cells to form filaments, antibiotics to kill live bacterial cells, and antibodies against free endotoxins.

Underlying the disclosed purification procedure is a discovery by the present inventors that, despite the difference of their bacterial sources, all intact minicells are approximately 400 nm in size, i.e., larger than membrane blebs and other smaller vesicles and yet smaller than parental bacteria. Size determination for minicells can be accomplished by using solid-state, such as electron microscopy, or by liquid-based techniques, e.g., dynamic light scattering. The size value yielded by each such technique can have an error range, and the values can differ somewhat between techniques. Thus, the size of minicells in a dried state can be measured via electron microscopy as approximately 400 nm±50 nm. On the other hand, dynamic light scattering can measure the same minicells to be approximately 500 nm±50 nm in size. Also, drug-packaged, ligand-targeted minicells can be measured, again using dynamic light scattering, to be approximately 500 nm±50 nm.

This scatter of size values is readily accommodated in practice, e.g., for purposes of isolating minicells from immunogenic components and other toxic contaminants, as described above. That is, an intact, bacterially derived minicell is characterized by cytoplasm surrounded by a rigid membrane, which gives the minicell a rigid, spherical structure. This structure is evident in transmission-electron micrographs, in which minicell diameter is measured, across the minicell, between the outer limits of the rigid membrane. This measurement provides the above-mentioned size value of 400 nm±50 nm.

Another structural element of a minicell derived from Gram-negative bacteria is the O-polysaccharide component of lipopolysaccharide (LPS), which is embedded in the outer membrane via the lipid A anchor. The component is a chain of repeat carbohydrate-residue units, with as many as 70 to 100 repeat units of four to five sugars per chain. Because these chains are not rigid, in a liquid environment, as in vivo, they can adopt a waving, flexible structure that gives the general appearance of seaweed in a coral sea environment; i.e., the chains move with the liquid while remaining anchored to the minicell membrane.

Influenced by the O-polysaccharide component, dynamic light scattering can provide a value for minicell size of about 500 nm as noted above. Nevertheless, minicells from Gram-negative and Gram-positive bacteria alike readily pass through a 0.45 m filter, which substantiates an effective minicell size of 400 nm±50 nm. The above-mentioned scatter in sizes is encompassed by the present invention and, in particular, is denoted by the qualifier "approximately" in the phrase "approximately 400 nm in size" and the like.

In relation to toxic contaminants, a composition of the disclosure can contain less than about 350 EU free endotoxin. Illustrative in this regard are levels of free endotoxin of about 250 EU, about 200 EU, about 150 EU, about 100 EU, about 90 EU, about 80 EU, about 70 EU, about 60 EU, about 50 EU, about 40 EU, about 30 EU, about 20 EU, about 15 EU, about 10 EU, about 9 EU, about 8 EU, about 7 EU, about 6 EU, about 5 EU, about 4 EU, about 3 EU, about 2 EU, about 1 EU, about 0.9 EU, about 0.8 EU, about 0.7 EU, about 0.6 EU, about 0.5 EU, about 0.4 EU, about 0.3 EU, about 0.2 EU, about 0.1 EU, about 0.05 EU, and about 0.01 EU, respectively.

A composition of the disclosure also can contain at least about $10^8$ minicells, e.g., at least about $5 \times 10^8$. Alternatively, the composition can contain on the order of about $10^9$ or about $10^{10}$ vesicles, e.g., about $5 \times 10^9$, about $1 \times 10^{10}$ or about $5 \times 10^{10}$ vesicles. Amongst any such number of minicells, moreover, a composition of the disclosure can contain fewer than about 10 contaminating live/parent bacterial cells, e.g., fewer than about 9, about 8, about 7, about 6, about 5, about 4, about 3, about 2, or about 1 live/parent bacterial cells.

b. Formulations

Pharmaceutical compositions suitable for use in the methods described herein can include the disclosed minicell delivery vectors and a pharmaceutically acceptable carrier or diluent.

The invention includes within its scope compositions, or formulations, comprising (a) an intact minicell and (b) a pharmaceutically acceptable carrier therefor, where the minicell contains at least one nucleic acid adjuvant molecule, a plasmid comprising a segment that encodes at least one nucleic acid adjuvant molecule, and/or at least one agonist of a nucleic acid sensor. The at least nucleic acid adjuvant or agonist of a nucleic acid sensor may comprise any of the nucleic acid adjuvants or agonists of nucleic acid sensors described herein, or a combination thereof.

In some embodiments, the formulation may also further comprise a drug, as described herein. Preferably, the minicell of the formulation contains the drug. Alternatively, the minicell may contain a nucleic acid molecule, such as a plasmid, that encodes the drug.

The minicell-containing formulations preferably contain fewer than about 1 contaminating parent bacterial cell per $10^7$ minicells, more preferably contain fewer than about 1 contaminating parent bacterial cell per $10^8$ minicells, even more preferably contain fewer than about 1 contaminating parent bacterial cell per $10^9$ minicells, still more preferably contain fewer than about 1 contaminating parent bacterial cell per $10^{10}$ minicells and most preferably contain fewer than about 1 contaminating parent bacterial cell per $10^{11}$ minicells.

The formulations also optionally contain a bispecific ligand for targeting the minicell to a target cell. The minicell and ligand may be any of those described herein. Thus, in some embodiments the minicell contains at least one nucleic acid adjuvant, a nucleic acid encoding a nucleic acid adjuvant, and/or at least one agonist of a nucleic acid sensor and a bispecific ligand that is capable of binding to a surface component of the minicell and to a surface component of a target mammalian cell.

A formulation comprising minicells and, optionally drugs and bispecific ligands, of the present disclosure can be formulated in conventional manner, using one or more pharmaceutically acceptable carriers or excipients.

Formulations may be presented in unit dosage form, e.g., in ampules or vials, or in multi-dose containers, with or without an added preservative. The formulation can be a solution, a suspension, or an emulsion in oily or aqueous vehicles, and may contain formulatory agents, such as suspending, stabilizing and/or dispersing agents. A suitable solution is isotonic with the blood of the recipient and is illustrated by physiological saline, Ringer's solution, and dextrose solution. Alternatively, formulations may be in lyophilized powder form, for reconstitution with a suitable vehicle, e.g., sterile, pyrogen-free water or physiological saline. The formulations also may be in the form of a depot preparation. Such long-acting formulations may be administered by implantation (for example, subcutaneously or intramuscularly) or by intramuscular injection.

In some embodiments, the disclosed minicell delivery vectors may be formulated to be administered concurrently with another therapeutic agent or drug. In some embodiments, the disclosed minicell delivery vectors may be formulated to be administered in sequence with another therapeutic agent or drug. For example, in some embodiments, the disclosed minicell delivery vectors may be administered either before or after the patient has received a treatment of chemotherapy for the treatment of cancer. Alternatively, in some embodiments the disclosed minicell delivery vectors may be administered either before or after the patient has received a vaccine to prevent an infection.

c. Administration Schedules

In general, the formulations disclosed herein may be used at appropriate dosages defined by routine testing, to obtain optimal physiological effect, while minimizing any potential toxicity. The dosage regimen may be selected in accordance with a variety of factors including age, weight, sex, medical condition of the patient; the severity of the condition to be treated, the route of administration, and the renal and hepatic function of the patient.

Optimal precision in achieving concentrations of minicell within the range that yields maximum efficacy with minimal side effects may require a regimen based on the kinetics of the minicell availability to target sites and target cells. Distribution, equilibrium, and elimination of a minicell or drug may be considered when determining the optimal concentration for a treatment regimen. The dosages of the minicells and drugs may be adjusted when used in combination, to achieve desired effects.

Moreover, the dosage administration of the formulations may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See, e.g., WO 00/67776.

Specifically, the formulations may be administered at least once a week over the course of several weeks. In some embodiment, the formulations are administered at least once a week over several weeks to several months. In some embodiment, the formulations are administered at least twice a week over several weeks to several months. In some embodiment, the formulations are administered at least three times a week over several weeks to several months. In some embodiment, the formulations are administered at least four times a week over several weeks to several months. In some embodiment, the formulations are administered at least five times a week over several weeks to several months. In some embodiment, the formulations are administered at least six times a week over several weeks to several months.

More specifically, the formulations may be administered at least once a day for about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days. Alternatively, the formulations may be administered about once every day, about once every 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days or more.

The formulations may alternatively be administered about once every week, about once every 2, 3, 4, 5, 6, 7, 8, 9, 10, 11, 12, 13, 14, 15, 16, 17, 18, 19 or 20 weeks or more. Alternatively, the formulations may be administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more.

Alternatively, the formulations may be administered about once every month, about once every 2, 3, 4, 5, 6, 7, 8, 9, 10, 11 or 12 months or more.

The formulations may be administered in a single daily dose, or the total daily dosage may be administered in divided doses of two, three, or four times daily.

In a method in which minicells are administered before another therapeutic agent or drug, administration of the therapeutic agent or drug may occur anytime from several minutes to several hours before or after administration of the minicells. The other therapeutic agent or drug may alternatively be administered anytime from several hours to several days, possibly several weeks up to several months before or after the minicells.

More specifically, the minicells may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 hours before or after another therapeutic agent or drug. Moreover, the minicells may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or about 31 days before or after the administration of another therapeutic agent or drug. In yet another embodiment, the minicells may be administered at least about 1, about 2, about 3, about 4, about 5, about 6, about 7, about 8, about 9, about 10, about 11, about 12, about 13, about 14, about 15, about 16, about 17, about 18, about 19 or about 20 weeks or more before or after the administration of another therapeutic agent or drug. In a further embodiment, the minicells may be administered at least about 1, about 2, about 3, about 4, about 5, about 6, about 7, about 8, about 9, about 10, about 11 or about 12 months before or after the administration of another therapeutic agent or drug.

Dosage regimens can be adjusted to provide the optimum desired response (e.g., a therapeutic response like tumor regression or remission). For example, in some embodiments, a single bolus of minicell delivery vectors may be administered, while in some embodiments, several divided doses may be administered over time or the dose may be proportionally reduced or increased as indicated by the situation. For example, in some embodiments the disclosed minicell delivery vectors may be administered once or twice weekly by subcutaneous, intramuscular, or intravenous injection. In some embodiments, the disclosed minicell delivery vectors may be administered once or twice monthly by subcutaneous, intramuscular, or intravenous injection. In some embodiments, the disclosed minicell delivery vectors may be administered once every week, once every other week, once every three weeks, once every four weeks, once every other month, once every three months, once every four months, once every five months, or once every six months.

Particular treatment regimens may be evaluated according to whether they will improve a given patient's outcome, meaning the treatment will reduce the risk of recurrence or increase the likelihood of progression-free survival of the given cancer or infection.

Thus, for the purposes of this disclosure, a subject is treated if one or more beneficial or desired results, including desirable clinical results, are obtained. For example, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

Furthermore, while the subject of the methods is generally a patient with some type of cancer or infection, the age of the patient is not limited. The disclosed methods are useful for treating tumors, cancer, malignant disease, or cancer cell proliferation with various recurrence and prognostic outcomes across all age groups and cohorts. The disclosed methods are also useful for treating or preventing various infections, including both bacterial and viral, either before or throughout the course of the infection. Further, in some embodiments, the subject may be a pediatric subject, while in other embodiments, the subject may be an adult subject.

3. Definitions

Unless defined otherwise, technical and scientific terms used herein have the meanings commonly understood by one of ordinary skill in the art, unless otherwise defined. Any suitable materials and/or methodologies known to those of ordinary skill in the art can be utilized in carrying out the methods described herein.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "sequence" refers to all or a portion of a polynucleotide or polypeptide sequence.

"Cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this invention particularly apply to precancerous, malignant, pre-metastatic, metastatic, and non-metastatic cells.

"Complementary" refers to the topological compatibility or matching together of the interacting surfaces of two molecules, such as base pairing in complementary nucleotide sequences. Thus, molecules can be described as complementary, and furthermore, the contact surface characteristics are complementary to each other.

"Cytokine" is a generic term for proteins released by one cell population that act on another cell population as intercellular mediators.

"Drug" refers to any physiologically or pharmacologically active substance that produces a local or systemic effect in animals, particularly mammals and humans.

"Expression" generally refers to the process by which a polynucleotide sequence undergoes successful transcription and translation such that detectable levels of the amino acid sequence or protein are expressed. In certain contexts herein, expression refers to the production of a nucleic acid sequence (i.e. a nucleic acid adjuvant), rather than the expression of a protein or amino acids. In other contexts, expression refers to the production of protein.

"Host cell" refers to a cell that may be, or has been, used as a recipient for a recombinant vector or other transfer of polynucleotides, and includes the progeny of the original cell that has been transfected. The progeny of a single cell may not necessarily be completely identical in morphology or in genomic or total DNA complement as the original parent due to natural, accidental, or deliberate mutation.

"Hybridization" refers to any process by which a polynucleotide sequence binds to a complementary sequence through base pairing.

As used herein, the phrases "therapeutically effective amount" means that a dose of the disclosed bead particles provides the specific pharmacological effect for which the drug is administered in a subject in need of such treatment, e.g., to reduce, ameliorate, or eliminate cancer/tumor growth, progression, or recurrence. It is emphasized that a therapeutically effective amount of a minicell containing a nucleic acid adjuvant or agonist of a nucleic acid sensor will not always be effective in treating the cancer/tumors of every individual subject, even though such dosage is deemed to be a therapeutically effective amount by those of skill in the art. Those skilled in the art can adjust what is deemed to be a therapeutically effective amount in accordance with standard practices as needed to treat a specific subject and/or specific type of disease, i.e., a given cancer or infection. The therapeutically effective amount may vary based on the route of administration and dosage form, the age and weight of the subject, and/or the subject's condition, including the progression, stage, and/or class of the disease at the time of treatment.

The terms "treatment" or "treating" refer to obtaining a desired pharmacological and/or physiologic effect on an active disease. For instance, the effect may be completely or partially reducing, ameliorating or eliminating a disease, for instance, inhibiting cancer/tumor growth and/or progression, or causing cancer/tumor cell death. "Treatment" covers any treatment of a disease in a mammal, particularly a human, and includes: (1) inhibiting a disease symptom, i.e., arresting its development; or (2) relieving the disease symptom, i.e., causing regression of the disease or symptom.

The terms "prevent" or "preventing" as used herein refer to preventing the disease or symptom from occurring in a subject, which may be predisposed to the disease or symptom and/or has not yet been diagnosed as having it. "Preventing" a disease can include stopping the formation of cancer/tumor cells or inhibiting the recurrence of cancer/tumor growth or prophylactically stopping an infection from taking hold in an individual.

"Individual," "subject," "host," and "patient," are used interchangeably herein, and refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Oligonucleotide" refers to a polynucleotide comprising, for example, from about 10 nucleotides (nt) to about 1000 nt. Oligonucleotides for use in the invention are preferably from about 10 nt to about 150 nt. The oligonucleotide may be a naturally occurring oligonucleotide or a synthetic oligonucleotide. Oligonucleotides may be modified.

"Minicell" refers to anucleate forms of bacterial cells, engendered by a disturbance in the coordination, during binary fission, of cell division with DNA segregation. Minicells are distinct from other small vesicles that are generated and released spontaneously in certain situations and, in contrast to minicells, are not due to specific genetic rearrangements or episomal gene expression. For practicing the present invention, it is desirable for minicells to have intact cell walls ("intact minicells").

"Modified oligonucleotide" and "Modified polynucleotide" refer to oligonucleotides or polynucleotides with one or more chemical modifications at the molecular level of the natural molecular structures of all or any of the bases, sugar moieties, internucleoside phosphate linkages, as well as to molecules having added substitutions or a combination of modifications at these sites. The internucleoside phosphate linkages may be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5' linkages, and combinations of such similar linkages. The phosphodiester linkage may be replaced with a substitute linkage, such as phosphorothioate, methylamino, methylphosphonate, phosphoramidate, and guanidine, and the ribose subunit of the polynucleotides may also be substituted (e.g., hexose phosphodiester; peptide nucleic acids). The modifications may be internal (single or repeated) or at the end(s) of the oligonucleotide molecule, and may include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e.g., 3'-substituted ribonucleotides or deoxyribonucleotide monomers), any of which are bound together via 5' to 3' linkages.

The phrase "nucleic acid molecules" and the term "polynucleotides" denote polymeric forms of nucleotides of any length, either ribonucleotides or deoxynucleotides. They include single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of a polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. A polynucleotide may be further modified, such as by conjugation with a labeling component. Other types of modifications include caps, substitution of one or more of the naturally occurring nucleotides with an analog, and introduction of means for attaching the polynucleotide to proteins, metal ions, labeling components, other polynucleotides, or a solid support.

"Pharmaceutically acceptable" refers to physiological compatibility. A pharmaceutically acceptable carrier or excipient does not abrogate biological activity of the composition being administered, is chemically inert and is not toxic to the organism in which it is administered.

"Polypeptide" and "protein," used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

"Purified" refers to a compound that is removed from its natural environment and is at least about 60%, about 65%, about 70%, about 75%, about 80%, about 85%, about 90%, about 91%, about 92%, about 93%, about 94%, about 95%, about 96%, about 97%, about 98%, about 99%, about 99.9%, or about 99.99% free from other components with which it is naturally associated.

"Sequence Identity" refers to a degree of similarity or complementarity. There may be partial identity or complete identity. A partially complementary sequence is one that at least partially inhibits an identical sequence from hybridizing to a target polynucleotide; it is referred to using the functional term "substantially identical." The inhibition of hybridization of the completely complementary sequence to the target sequence may be examined using a hybridization assay (Southern or Northern blot, solution hybridization, and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

Another way of viewing sequence identity, in the context to two nucleic acid or polypeptide sequences, entails referencing residues in the two sequences that are the same when aligned for maximum correspondence over a specified region. As used here, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

The compositions and methods of the disclosure may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

REFERENCES

Alexopoulou, L., Holt, A. C., Medzhitov, R. & Flavell, R. A., Recognition of double-stranded RNA and activation of NF-κB by Toll-like receptor 3. Nature 413, 732-738 (2001).

Ammi, R. et al., Poly(I:C) as cancer vaccine adjuvant: knocking on the door of medical breakthroughs. Pharmacol. Ther. 140, 120-131 (2014).

Blasius, A. L. & Beutler, B., Intracellular toll-like receptors. Immunity 32, 305-315 (2010).

Brazda V, Coufal J, Liao J C, Arrowsmith C H., Preferential binding of IFI16 protein to cruciform structure and superhelical DNA. Biochem Biophys Res Commun. 422, 716-720 (2012).

Costa S, Borgogna C, Mondini M, De Andrea M, Meroni P L, Berti E, et al., Redistribution of the nuclear protein IFI16 into the cytoplasm of ultraviolet B-exposed keratinocytes as a mechanism of autoantigen processing. Br J Dermatol. 164, 282-90 (2011).

Dawson M J, Trapani J A., The interferon-inducible autoantigen, IFI 16: localization to the nucleolus and identification of a DNA-binding domain. Biochem Biophys Res Commun. 214, 152-62 (1995).

Diner, B. A., Li, T., Greco, T. M., Crow, M. S., Fuesler, J. A., Wang, J., and Cristea, I. M., The functional interactome of PYHIN immune regulators reveals IFIX is a sensor of viral DNA. Mol. Syst. Biol. 11, 787 (2015).

Diner, B A., Lum K K., Cristea, I M., The emerging role of nuclear viral DNA sensors. J. Biol. Chem. 290, 26412-26421 (2015).

Field, A. K., Tytell, A. A., Lampson, G. P. & Hilleman, M. R., Inducers of interferon and host resistance. II. Multistranded synthetic polynucleotide complexes. Proc. Natl Acad. Sci. USA 58, 1004-1010 (1967).

Gao, P. et al., Cyclic [G(2',5')pA(3',5')p] is the metazoan second messenger produced by DNA-activated cyclic GMP-AMP synthase. Cell 153, 1094-1107 (2013).

Gitlin, L. et al., Essential role of mda-5 in type I IFN responses to polyriboinosinic:polyribocytidylic acid and encephalomyocarditis picornavirus. Proc. Natl Acad. Sci. USA 103, 8459-8464 (2006).

Goff, P. H. et al., Synthetic TLR4 and TLR7 ligands as influenza virus vaccine adjuvants induce rapid, sustained and broadly protective responses. J. Virol. 89, 3221-3335 (2015).

Goubau, D. et al., Antiviral immunity via RIG-I-mediated recognition of RNA bearing 5'-diphosphates. Nature 514, 372-375 (2014).

Haronikova L, Coufal J, Kejnovska I, Jagelska E B, Fojta M et al., IFI16 Preferentially Binds to DNA with Quadruplex Structure and Enhances DNA Quadruplex Formation. PLoS One 11, 1-19 (2016).

Hemmi, H. et al., Small anti-viral compounds activate immune cells via the TLR7 MyD88-dependent signaling pathway. Nat. Immunol. 3, 196-200 (2002).

Hornung, V. et al., 5'-triphosphate RNA is the ligand for RIG-I. Science 314, 994-997 (2006).

Hornung, V., SnapShot: nucleic acid immune sensors, part 1. Immunity 41, 868-868.e1 (2014).

Hou, F. et al., MAVS forms functional prion-like aggregates to activate and propagate antiviral innate immune response. Cell 146, 448-461 (2011).

Huen, A. O. & Rook, A. H., Toll receptor agonist therapy of skin cancer and cutaneous T-cell lymphoma. Curr. Opin. Oncol. 26, 237-244 (2014).

Jin T, Perry A, Jiang J, Smith P, Curry J A, Unterholzner L, et al., Structures of the HIN domain:DNA complexes reveal ligand binding and activation mechanisms of the AIM2 inflammasome and IFI16 receptor. Immunity. 36, 561-571 (2012).

Junt, T., Barchet, W., Translating nucleic acid-sensing pathways into therapies. Nat Rev Immunol. 15, 529-544 (2015).

Kato, H. et al., Length-dependent recognition of double-stranded ribonucleic acids by retinoic acid-inducible gene-I and melanoma differentiation-associated gene 5. J. Exp. Med. 205, 1601-1610 (2008).

Krieg, A. M. et al., CpG motifs in bacterial DNA trigger direct B-cell activation. Nature 374, 546-549 (1995).

Li, X.-D. et al., Pivotal roles of cGAS-cGAMP signaling in antiviral defense and immune adjuvant effects. Science 341, 1390-1394 (2013).

Li, T., Chen, J., and Cristea, I. M., Human cytomegalovirus tegument protein pUL83 inhibits IFI16-mediated DNA sensing for immune evasion. Cell Host Microbe 14, 591-599 (2013).

Li, T., Diner, B. A., Chen, J., and Cristea, I. M., Acetylation modulates cellular distribution and DNA sensing ability of interferon-inducible protein IFI16. Proc. Natl. Acad. Sci. U.S.A. 109, 10558-10563 (2012).

Ohto, U. et al., Structural basis of CpG and inhibitory DNA recognition by Toll-like receptor 9. Nature 520, 702-705 (2015).

Orzalli, M. H., DeLuca, N. A., and Knipe, D. M., Nuclear IFI16 induction of IRF-3 signaling during herpesviral infection and degradation of IFI16 by the viral ICP0 protein. Proc. Natl. Acad. Sci. U.S.A. 109, E3008-E3017 (2012).

Pichlmair, A. et al., Activation of MDA5 requires higher-order RNA structures generated during virus infection. J. Virol. 83, 10761-10769 (2009).

Quintieri, L., Geroni, C., Fantin, M., Battaglia, R., Rosato, A., Speed, W., Zanovello, P., Floreani, M., Formation and Antitumor Activity of PNU-159682, A Major Metabolite of Nemorubicin in Human Liver Microsomes. Clin. Cancer Res. 11, 1608-1617 (2005).

Sun, L., Wu, J., Du, F., Chen, X. & Chen, Z. J., Cyclic GMP-AMP synthase is a cytosolic DNA sensor that activates the type I interferon pathway. Science 339, 786-791 (2013).

Tanji, H. et al., Toll-like receptor 8 senses degradation products of single-stranded RNA. Nat. Struct. Mol. Biol. 22, 109-115 (2015).

Temizoz, B. et al., TLR9 and STING agonists synergistically induce innate and adaptive type II IFN. Eur. J. Immunol. 45, 1159-1169 (2015).

Thompson M R, Sharma S, Atianand M, Jensen S B, Carpenter S, Knipe D M, et al., Interferon gamma inducible protein (IFI) 16 transcriptionally regulates type i interferons and other interferon-stimulated genes and controls the interferon response to both DNA and RNA viruses. J Biol Chem. 289, 23568-81 (2014).

Unterholzner L, Keating S E, Baran M, Horan K A, Jensen S B, Sharma S, et al., IFI16 is an innate Immune sensor for intracellular DNA. Nat Immunol. 11, 997-1004 (2010).

Wu, J. et al., Cyclic GMP-AMP is an endogenous second messenger in innate immune signaling by cytosolic DNA. Science 339, 826-830 (2013).

The following examples are given to illustrate the present disclosure. It should be understood that the invention is not to be limited to the specific conditions or details described in these examples.

EXAMPLES

Example 1—Significantly Enhanced Tumor Regression Following Treatment with $^{EGFR}$Minicells$_{PNU\text{-}159682}$ and Minicells$_{40\text{-}mer}$ This example demonstrates that combined treatment of mouse xenografts with bispecific ligand-targeted and PNU-159682-packaged intact minicells with non-targeted, 40-mer-packaged intact minicells can enhance anti-tumor efficacy as compared to treatment with the former alone.

Minicells were obtained from an *S. typhimurium* minCDE-mutant strain and were purified using a gradient centrifugation/filamentation/filtration/endotoxin removal procedure as previously described (MacDiarmid et al. (2007)). The purified minicells were packaged with the chemotherapeutic drug doxorubicin-derivative, PNU-159682 (Quintieri et al. (2005)) or double stranded 40 nucleotide long RNA (40-mer) as described (MacDiarmid et al. (2007), (2009)).

The bispecific antibody (BsAb) used for targeting the minicells was a single polypeptide containing binding specificity for both the *S. typhimurium* O-polysaccharide (present on minicells) and for human EGFR (overexpressed on alveolar adenocarcinoma cells A549). The O-polysaccharide specificity was derived from a mouse monoclonal antibody, for which the variable regions were isolated from the hybridoma cell line 1H10 and presented as a single-chain variable fragment (scFv). The EGFR specificity, also presented as a scFv, was derived from the commercial antibody VECTIBIX® (Amgen, USA). The two scFv components were separated by flexible linker, and a 6×His tag incorporated at the N-terminus to facilitate purification by immobilised metal affinity chromatography, and a c-myc tag at the C-terminus to aid in additional detection. The DNA vector encoding the BsAb contained a hCMV promoter for high level expression and a signal peptide for the secretion of the BsAb into the cell culture medium. The expression vector encoding the BsAb was stably transfected into suspension adapted Chinese hamster ovary (CHO) cells in chemically defined, protein and animal origin free medium and the protein is expressed over 10 days in culture.

The two chromatographic columns were used to purify the antibody and are an immobilized metal ion affinity chromatography (IMAC—HisTrap Excel column) and hydroxyapatite chromatography (BioRad CHT I column), which provided final antibody purity of >98%. For viral safety of product, the antibody went through a solvent/detergent inactivation (using TNBP/Tween) and a viral filtration. The final yield of antibody was 10 mg from 1 L of cell culture supernatant.

The mice (6 week old female athymic nude mice) used in this example were purchased from Animal Resources Centre, Perth, WA, Australia, and all animal experiments were performed in compliance with the guide of care and use of laboratory animals and with Animal Ethics Committee approval. The experiments were performed in the NSW Agriculture accredited small animal facility at EnGeneIC Pty Ltd (Sydney, NSW, Australia). Human alveolar adenocarcinoma cells (A549, ATCC) were grown in tissue culture to full confluency in T-75 flasks in RPMI 1640 medium supplemented with 5% Bovine Calf Serum (GIBCO-BRL Life Technologies, Invitrogen Corporation, Carlsbad, Calif., USA) and glutamine (Invitrogen) in a humidified atmosphere of 95% air and 5% $CO_2$ at 37° C.

$1\times10^6$ cells in 50 μL serum-free media together with 50 μL growth factor reduced matrigel (BD Biosciences, Franklin Lakes, N.J., USA) were injected subcutaneously between the shoulder blades of each mouse using a 23-gauge needle. The tumors were measured twice a week using an electronic digital caliper (Mitutoyo, Japan, precision to 0.001) and mean tumor volume was calculated using the formula, length (mm)×width$^2$ (mm)×0.5=volume (mm$^3$). The treatments were commenced when the tumors reached a mean of ~285 mm$^3$ and mice were randomized to four different groups of 7 mice per group. All treatments were administered intravenously (i.v.) in a total volume of 100 μl. All minicell doses contained $1\times10^9$ minicells of the respective type.

The experiment was designed as follows. Group 1 (control) received no sterile physiological saline. Group 2 $^{EGFR}$minicells$_{PNU\text{-}159682}$, Group 3 $^{EGFR}$minicells$_{PNU\text{-}159682}$+minicells$_{40\text{-}mer}$.

Figure 3:
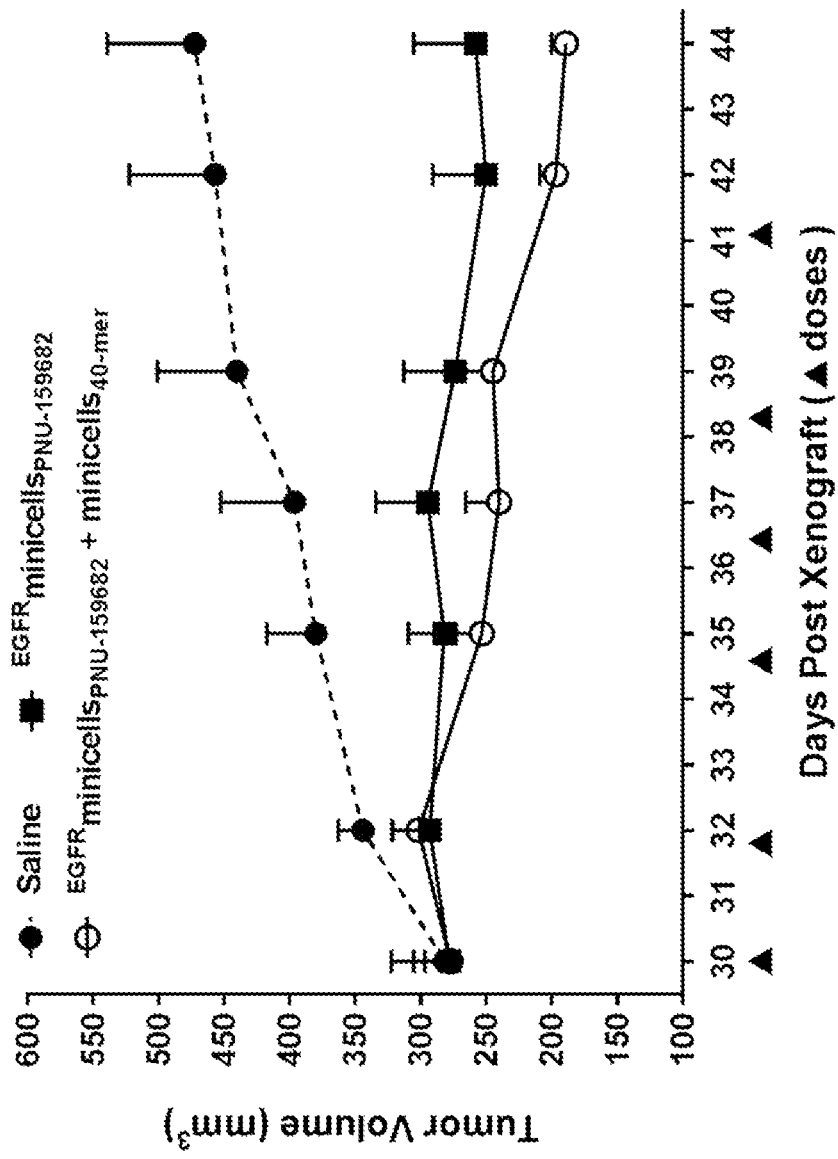
FIG. 3 shows the results of an in vivo study comparing the efficacy of drug-packaged minicells alone to a combination treatment of drug-(PNU159682) and nucleic acid adjuvant-(40-mer) packaged minicells in a mouse xenograft tumor model. As shown in the figure, mice receiving $^{EGFR}$minicells$_{PNU\text{-}159682}$+minicells$_{40\text{-}mer}$ (Group 3) showed highly significant tumor regression by day 44 after a total of 6 doses, while mice receiving $^{EGFR}$minicells$_{PNU\text{-}159682}$ alone (Group 2) were merely stable. Group 1 represents the control mice that received only saline.

The results revealed (FIG. 3) that mice treated with $^{EGFR}$minicells$_{PNU\text{-}159682}$ (Group 2) achieved tumor stabilization. In contrast, mice treated with $^{EGFR}$minicells$_{PNU\text{-}159682}$+minicells$_{40\text{-}mer}$ (Group 3) showed highly significant tumor regression by day 44 after a total of 6 doses.

These results demonstrate the effectiveness of the nucleic acid adjuvants according to the invention, as the therapeutic results were significantly better with use of the adjuvant as compared to treatment with non-adjuvanted drug.

Example 2—Significantly Enhanced Tumor Regression Following Treatment with $^{EGFR}$Minicells$_{PNU\text{-}159682}$ and Minicells$_{40\text{-}mer}$ or Minicells$_{50\text{-}mer}$ This example demonstrates that combined treatment of mouse xenografts with bispecific ligand-targeted and PNU-159682-packaged intact minicells with non-targeted, 40-mer- or 50-mer-packaged intact minicells can enhance anti-tumor efficacy as compared to treatment with the former alone.

The various minicells were prepared as described in Example 1. Seven mice per group were prepared for the A549 xenograft as described in Example 1.

The experiment was designed as follows. Group 1 (control) received no sterile physiological saline. Group 2 $^{EGFR}$minicells$_{PNU-159682}$, Group 3 $^{EGFR}$minicells$_{PNU-159682}$+minicells$_{40-mer}$, Group 4 $^{EGFR}$minicells$_{PNU-159682}$+minicells$_{50-mer}$, Group 5 $^{EGFR}$minicells$_{PNU-159682}$+minicells.

Figure 4:
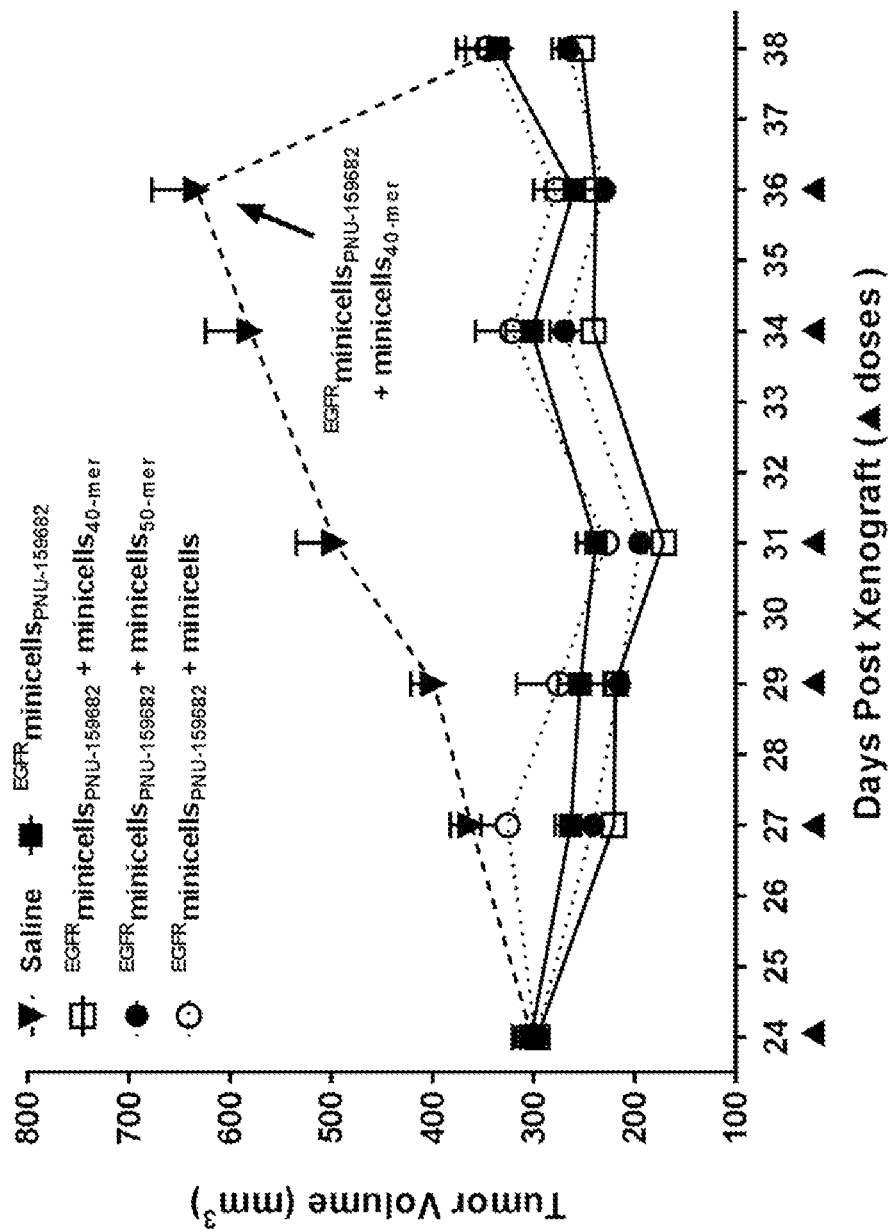
FIG. 4 shows results from a comparison of anti-tumor efficacy of nucleic acid adjuvant 40-mers and 50-mers in a mouse xenograft model. Group 1 (control) received sterile physiological saline. The other groups were administered as follows: Group 2 $^{EGFR}$minicells$_{PNU\text{-}159682}$, Group 3 $^{EGFR}$minicells$_{PNU\text{-}159682}$+minicells$_{40\text{-}mer}$, Group 4 $^{EGFR}$minicells$_{PNU\text{-}159682}$+minicells$_{50\text{-}mer}$, Group 5 $^{EGFR}$minicells$_{PNU\text{-}159682}$+minicells.

The results revealed (FIG. 4) that mice treated with $^{EGFR}$minicells$_{PNU-159682}$ (Group 2) and $^{EGFR}$minicells$_{PNU-159682}$+minicells (Group 5) achieved tumor stabilization. In contrast, mice treated with $^{EGFR}$minicells$_{PNU-159682}$+minicells$_{40-mer}$ (Group 3) or with $^{EGFR}$minicells$_{PNU-159682}$+minicells$_{50-mer}$ (Group 4) showed significant enhancement of tumor regression by day 38 after a total of 6 doses. Of further interest, when the saline treated mice had developed large tumor volumes (~600 mm$^3$) by day 36 and the treatment was changed to $^{EGFR}$minicells$_{PNU-159682}$+minicells$_{40-mer}$, the tumor volumes plummeted to ~300 mm$^3$ by day 38. This is a dramatic 50% decrease in tumor volume over a 2 day period.

These results demonstrate the effectiveness of the nucleic acid adjuvants according to the invention, as the therapeutic results were significantly better with use of the adjuvant as compared to treatment with non-adjuvanted drug.

Example 3—Prophetic Human Treatment

This example illustrates methods using the disclosed minicell delivery vectors in the treatment of cancer.

A patient known to have or suspected of having cancer is administered a therapeutically effective amount of a bacterially-derived minicell delivery vector comprising at least one nucleic acid adjuvant or agonist of a nucleic acid sensor, by intravenous, intramuscular, or subcutaneous injection. The patient is evaluated for the presence and/or severity of signs and symptoms associated with cancer, including, but not limited to, pain, weakness, tumor size, etc., and the patient is treated until one or more signs/symptoms are reduced, ameliorated, or eliminated.

Optionally, samples may be taken from the patient to monitor cancer progression following treatment. Optionally, another dose of the bacterially-derived minicell delivery vector comprising at least one nucleic acid adjuvant or agonist of a nucleic acid sensor is administered if signs/symptoms persist and/or if the cancer progresses or recurs.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure. All public documents referenced herein, including but not limited to published patent documents, are specifically incorporated by reference.

What is claimed:
1. A composition comprising:
 (a) an intact bacterial minicell, comprising:
  at least one nucleic acid adjuvant molecule packaged within the intact bacterial minicell at a therapeutically effective concentration that produces an immune response from a target cell in a subject, wherein the packaging is effected by co-incubating the minicell with the nucleic acid adjuvant in a buffer, wherein the intact bacterial minicell is plasmid-free,
  and
 (b) a pharmaceutically acceptable carrier therefor,
 wherein the at least one nucleic acid adjuvant molecule is linear double stranded RNA and has a length from about 40 nucleotides to about 50 nucleotides.

2. The composition of claim 1, wherein the immune response from the target cell comprises the production of Type I interferon.

3. The composition of claim 1, wherein the at least one nucleic acid adjuvant comprises a nucleic acid that binds to at least one of TLR3, RIG-I, or MDA5.

4. The composition of claim 1, wherein:
 (a) the intact minicell comprises at least two nucleic acid adjuvant molecules; and/or
 (b) the intact minicell comprises a nucleic acid adjuvant molecule and an agonist of a nucleic acid sensor.

5. The composition of claim 1, wherein the at least one nucleic acid adjuvant molecule comprises a sequence of 40 nucleotides or 50 nucleotides.

6. The composition of claim 1, wherein the at least one nucleic acid adjuvant molecule comprises a poly(I:C) or poly-ICLC.

7. The composition of claim 1, further comprising a bispecific ligand.

8. The composition of claim 7, wherein the bispecific ligand comprises a first arm that carries specificity for a minicell surface structure and a second arm that carries specificity for a non-phagocytic mammalian cell surface receptor.

9. The composition of claim 1, wherein the composition comprises fewer than about 1 contaminating parent bacterial cell per 107 minicells.

10. The composition of claim 2, wherein Type I interferon comprises interferon-α or interferon-β.

11. The composition of claim 5, wherein the at least one nucleic acid adjuvant molecule is a 40-mer.

12. The composition of claim 5, wherein the at least one nucleic acid adjuvant molecule is a 50-mer.

13. The composition of claim 7, wherein the bispecific ligand comprises a first arm that carries specificity for a minicell surface structure and a second arm that carries specificity for a non-phagocytic mammalian cell surface receptor, wherein the minicell surface structure is an O-polysaccharide component of a lipopolysaccharide on the minicell surface.

14. The composition of claim 7, wherein the bispecific ligand comprises a first arm that carries specificity for a minicell surface structure and a second arm that carries specificity for a non-phagocytic mammalian cell surface receptor, wherein the mammalian cell surface receptor is capable of activating receptor-mediated endocytosis of the minicell.

15. The composition of claim 7, wherein the bispecific ligand comprises an antibody or antibody fragment.

16. The composition of claim 1, wherein the composition comprises fewer than about 1 contaminating parent bacterial cell per 108 minicells.

17. The composition of claim 1, wherein the composition comprises fewer than about 1 contaminating parent bacterial cell per 109 minicells.

18. The composition of claim 1, wherein the composition comprises fewer than about 1 contaminating parent bacterial cell per 1010 minicells.

19. The composition of claim 1, wherein the composition comprises fewer than about 1 contaminating parent bacterial cell per $10^{11}$ minicells.

20. The composition of claim 4, wherein the agonist of a nucleic acid sensor comprises imiquimod or imidazoquinoline resiquimod.

21. The composition of claim 1, comprising at least about $5\times10^{8}$ minicells.

\* \* \* \* \*